(12) United States Patent
Takahara et al.

(10) Patent No.: US 6,620,916 B1
(45) Date of Patent: *Sep. 16, 2003

(54) MODIFIED PHYSIOLOGICALLY ACTIVE PROTEINS AND MEDICINAL COMPOSITIONS CONTAINING THE SAME

(75) Inventors: Yoshiyuki Takahara; Haruya Sato; Eiko Hayashi; Masanobu Yatagai; Manabu Suzuki; Tomoyuki Tabata; Chieko Ejima, all of Kawasaki (JP)

(73) Assignee: Ajinomoto Co., Inc., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 196 days.

(21) Appl. No.: 09/068,987
(22) PCT Filed: Sep. 26, 1997
(86) PCT No.: PCT/JP97/03435
§ 371 (c)(1), (2), (4) Date: Sep. 25, 1998
(87) PCT Pub. No.: WO98/13381
PCT Pub. Date: Apr. 2, 1998

(30) Foreign Application Priority Data

Sep. 26, 1996 (JP) .............................. 8-273922

(51) Int. Cl.[7] .............................................. C07K 14/52
(52) U.S. Cl. ................ 530/402; 530/351; 530/395; 530/399; 530/402; 530/324; 435/41; 435/68.1; 514/2; 514/8; 514/12
(58) Field of Search ................................ 530/324, 395, 530/399, 402, 351; 435/41, 68.1

(56) References Cited

U.S. PATENT DOCUMENTS

| 4,632,780 A | * | 12/1986 | Seidah | 530/306 |
| 5,124,437 A | * | 6/1992 | Akaike | 530/322 |
| 5,639,734 A | * | 6/1997 | Esko | 514/25 |
| 5,770,420 A | * | 6/1998 | Lowe | 435/193 |
| 5,843,713 A | * | 12/1998 | Yoshida | 435/69.1 |
| 6,010,871 A | * | 1/2000 | Takahara | 435/68.1 |
| 6,322,996 B1 | | 11/2001 | Sato et al. | 435/68.1 |

FOREIGN PATENT DOCUMENTS

JP 8-89278 7/1996

OTHER PUBLICATIONS

Abstract of JP 5-202085, 1993.*
Ashwell, Annual Review of Biochemistry 51, 531-554, 1982*

* cited by examiner

Primary Examiner—Christopher S. F. Low
Assistant Examiner—David Lukton
(74) Attorney, Agent, or Firm—Oblon, Spivak, McClelland, Maier & Neustadt, P.C.

(57) ABSTRACT

The present invention relates to a modified physiologically active protein, modified physiologically active proteins produced by the process and pharmaceutical compositions containing the same.

26 Claims, 14 Drawing Sheets

| BIOCHEMICAL ITEMS | 1. SALINE | 2. rhIL-2(1.5μg/day) | 3. rhIL-2(4.4μg/day) | 4. rhIL-2(13.3μg/day) | 5. rhIL-2(40μg/day) |
|---|---|---|---|---|---|
| LIVER WEIGHT(w/w%) | 4.30 ± 0.31 | 4.48 ± 0.24 | 4.66 ± 0.34 | 4.91 ± 0.58 | 5.07 ± 0.11* |
| LUNG WEIGHT(w/w%) | 0.57 ± 0.02 | 0.58 ± 0.04 | 0.58 ± 0.05 | 0.64 ± 0.05 | 0.72 ± 0.01* |
| KIDNEY WEIGHT(w/w%) | 0.56 ± 0.06 | 0.56 ± 0.02 | 0.59 ± 0.07 | 0.58 ± 0.01 | 0.58 ± 0.06 |

| BIOCHEMICAL ITEMS | 6. (Gal)3-rhIL-2(1.5μg/day) | 7. (Gal)3-rhIL-2(4.4μg/day) | 8. (Gal)3-rhIL-2(13.3μg/day) | 9. (Gal)3-rhIL-2(40μg/day) |
|---|---|---|---|---|
| LIVER WEIGHT(w/w%) | 4.42 ± 0.79 | 4.53 ± 0.33 | 4.54 ± 0.32 | 5.15 ± 0.29* |
| LUNG WEIGHT(w/w%) | 0.55 ± 0.11 | 0.58 ± 0.06 | 0.58 ± 0.06 | 0.61 ± 0.06 |
| KIDNEY WEIGHT(w/w%) | 0.56 ± 0.08 | 0.57 ± 0.04 | 0.58 ± 0.06 | 0.57 ± 0.08 |

FIG. 11

| MEASURING ITEMS | 1. SALINE | 2. rhIL-2(1.5μg/day) | 3. rhIL-2(4.4μg/day) | 4. rhIL-2(13.3μg/day) | 5. rhIL-2(40μg/day) |
|---|---|---|---|---|---|
| GOT(U/L) | 53.0 ± 19.5 | 52.3 ± 15.2 | 52.7 ± 7.1 | 63.0 ± 20.0 | 83.3 ± 10.0 |
| GPT(U/L) | 26.0 ± 1.0 | 36.7 ± 8.0 | 36.3 ± 10.5 | 33.0 ± 7.9 | 53.0 ± 8.2* |
| TBIL-S(mg/mL) | 0.67 ± 0.06 | 0.80 ± 0.10 | 0.73 ± 0.15 | 0.77 ± 0.06 | 1.23 ± 0.06* |
| ALB-S(g/dL) | 2.63 ± 0.25 | 2.63 ± 0.15 | 2.47 ± 0.21 | 2.53 ± 0.21 | 2.40 ± 0.10 |
| TP-S(g/dL) | 4.90 ± 0.17 | 5.00 ± 0.20 | 4.67 ± 0.31 | 4.77 ± 0.31 | 4.73 ± 0.12 |
| BUN-S(mg/dL) | 25.0 ± 1.5 | 26.7 ± 1.0 | 26.3 ± 5.7 | 28.5 ± 6.7 | 27.8 ± 4.3 |

| MEASURING ITEMS | 6. (Gal)3-rhIL-2(1.5μg/day) | 7. (Gal)3-rhIL-2(4.4μg/day) | 8. (Gal)3-rhIL-2(13.3μg/day) | 9. (Gal)3-rhIL-2(40μg/day) |
|---|---|---|---|---|
| GOT(U/L) | 60.0 ± 21.7 | 47.0 ± 2.6 | 59.0 ± 18.5 | 55.7 ± 5.9 |
| GPT(U/L) | 34.3 ± 4.0 | 23.7 ± 6.7 | 34.3 ± 14.0 | 34.3 ± 4.9* |
| TBIL-S(mg/mL) | 0.97 ± 0.38 | 0.80 ± 0.00 | 1.03 ± 0.32 | 0.93 ± 0.32 |
| ALB-S(g/dL) | 2.83 ± 0.31 | 2.83 ± 0.21 | 2.73 ± 0.35 | 2.67 ± 0.15 |
| TP-S(g/dL) | 5.17 ± 0.51 | 5.00 ± 0.36 | 4.87 ± 0.35 | 5.00 ± 0.52 |
| BUN-S(mg/dL) | 27.7 ± 3.9 | 33.3 ± 4.1 | 26.4 ± 8.5 | 27.1 ± 7.0 |

FIG. 12

SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Pro Lys Pro Gln Gln Phe Met
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Arg Pro Lys Pro Gln Gln Phe Gly Leu
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Arg Pro Lys Pro Gln Gln Phe Met
1               5

MODIFIED PHYSIOLOGICALLY ACTIVE PROTEINS AND MEDICINAL COMPOSITIONS CONTAINING THE SAME

TECHNICAL FIELD

The present invention relates to a modified protein which has a liver accumulation property that its binding affinity for an asialoglycoprotein receptor present on a surface of a hepatocyte is lower than that of an asialoorosomucoid, and which can be produced by reacting a physiologically active protein containing one Gln residue that becomes a substrate for a transglutaminase with a branched-chain ligand composed of an amino acid derivative containing branched Gal or branched GalNAc in the presence of a transglutaminase to form an amide bond between the γ-carboxyamide group of the glutamine residue in the physiologically active protein and the terminal primary amino group in the branched-chain ligand, a process for producing the same, and a pharmaceutical composition containing the above-mentioned protein.

The modified protein of the present invention is useful as an active ingredient of medications since the physiologically active protein used as a starting material retains a physiological activity.

TECHNICAL BACKGROUND

In recent years, as a result of the development of the biotechnology, a variety of physiologically active proteins can be mass-produced, and they have been expected to be candidate substances of new medications. However, there have been a large number of problems to be solved in order to put the same into practical use. Of these, the strict control of the pharmacokinetics thereof has been considered to be an important subject for increasing therapeutic effects and reducing side effects. For example, a great many investigations have been conducted on antitumor effects of recombinant human interleukin-2 (rhIL-2). The effects are identified with respect to mouse sarcoma and mammary tumor, and antitumor effects to melanoma and hemangioendothelioma are clinically identified. However, no expected effects to solid carcinoma of digestive organs are identified with rhIL-2 alone either in the animal test or clinically. Further, since rhIL-2 has a short half-life in the blood after the intravenous administration, a high dose thereof is required to exhibit the antitumor activity. Nevertheless, when rhIL-2 is administered at a high dose, a serious side effect called capillary leak syndrome occurs, providing an. influence such as an edema or the like in the lung or the liver. It is necessary to control the chemotherapeutic fate thereof for increasing the therapeutic effect of rhIL-2. In order to solve such a problem, investigations have been lately conducted with respect to an immunotherapy on metastatic and primary liver cancers by accumulating rhIL-2 around liver sinusoidal cells using IL-2 preparations of rhIL-2-containing liposomes or galactose-containing liposomes and increasing an activity of liver sinusoidal lymphocytes or the like (Jpn. J. Cancer Chemother., (1994), 21(13), 2105–2107).

Meanwhile, it is known that mammallian hepatocytes have an asialoglycoprotein receptor (hereinafter abbreviated as "ASGR") which is a specific membrane-binding receptor to a glycoprotein having galactose (hereinafter abbreviated as "Gal") or N-acetylgalactosamine (hereinafter abbreviated as "GalNAc") in a branched sugar chain terminal (Ashwell, G., et al., Annu. Rev. Biochem., 1982, 51, 531–554). An uptake mechanism of the sugar protein with the receptor has a high binding affinity and is strong. In view of these properties and the specific presence of ASGR in hepatocytes, the above-mentioned receptor has attracted attention as a targeting system for specifically delivering medicines or genetic DNAs in metabolically important target cells (Wu, G. Y. et al., J. Biol. Chem., (1987), 262, 4429–4432).

As a result of studies on the structure-activity interrelation of branched oligosaccharide chains or synthetic Gal derivatives isolated in the sugar recognition mechanism with the above-mentioned receptor, it has been clarified in view of the distance between Gal residues and the branching pattern that the intensity of the binding affinity is in the order of tetra-antenna type Gal>tri-antenna type Gal>bi-antenna type Gal>mono-antenna type Gal (Lee, Y. C. et al., J. Biol. Chem., (1983), 258, 199–202; Kawaguchi, K. et al., Arch. Biochem. Biophys., (1980), 205, 388–395; Connolly D. T. et al., J. Biol. Chem., (1982), 257, 939–945; Lee, R. T., et al., Biochemistry, (1984), 23, 4255–4259).

According to these findings, attempts have been made to accumulate DNAs or liposomes in the liver using a synthetic ligand containing branched Gal or GalNAc and to incorporate the same into cells (Japanese Laid-Open (Kokai) No. 202,085/1993; Haensler J. et al., Bioconjugate Chem., (1993), 4, 85–93; and Merwin, J. R., Bioconjugate Chem., (1994), 5, 612–620).

However, in the drug delivery system (hereinafter abbreviated as "DDS") using an endocytosis mechanism through such a receptor, a low efficiency of intracellular uptake into the cells through a synthetic ligand is at issue. It has been made clear that this is because the binding affinity of such a synthetic ligand for ASGR is lower than a sugar chain of a glycoprotein such as asialoorosomucoid (ASOR), asialofetuin or the like which is a natural ligand [Lee, R. T. et al., Glycoconjugate J., (1987) 4, 317–328; and Biessen, E. A. L. et al., J. Med. Chem., 1995, 38, 1538–1546). Because of the low binding affinity, the synthetic ligand having Gal or GalNAc cannot be bound well to ASGR, and it is hard to incorporate ASGR into hepatocytes. Thus, the pharmaceutical effect is not exhibited well.

On the other hand, we have developed a method in which a protein is site-specifically modified with alkylamine derivatives of various compounds using an animal transglutaminase. Nevertheless, in this method, it is difficult that alkylamine derivatives are bound to a glutamine residue in an amino acid sequence of a physiologically active protein, for example, rhIL-2. Thus, a modified compound in which the alkylamine derivative is bound to the physiologically active protein derivative by introducing a peptide having a glutamine residue which is bindable using an animal transglutaminase into the physiologically active protein (PCT/JP 95/00298 (WO 96/06181)).

We have further investigated that the glutamine residue in the amino acid sequence of the physiologically active protein can be site-specifically modified using, among transglutaminases, especially a transglutaminase (B-TG) derived from microorganisms and having a wide substrate specificity to a Gln residue of a protein and using polylysine or alkylamine derivatives of an polyalkylene glycol such as polyethylene glycol without newly introducing a peptide molecule into an amino acid sequence of a physiologically active protein such as rhIL-2 or the like (Japanese Patent Application No. 270,102/1994 (Japanese Laid-Open (Kokai) No. 89,278/1996)); and PCT/JP 95/01994 (WO 96/10089)).

The present inventors have conducted various investigations to solve the problems that the compound modified with the synthetic ligand has a low affinity for ASGR and the modified compound is hardly incorporated into hepatocytes, and that for producing such a compound modified with the synthetic ligand, a peptide having a Gln residue has to be bound to a physiologically active protein.

The present inventors have attracted attention to the fact that if the physiologically active protein modified with such a synthetic ligand can directly act on cells other than hepatocytes, for examples, liver sinusoidal lymphocytes to exhibit the pharmaceutical effect of the physiologically active protein, the physiologically active proteins such as cytokine and the like are accumulated in the liver rather utilizing the low binding affinity for hepatocytes provided by such a synthetic ligand-modified compound, and that since the physiologically active substance is hardly incorporated into hepatocytes, it can be maintained in the liver, with the result that the activity of cytokine is expected to be exhibited by being bound to a specific receptor present on a cell membrane of the other target cell in the liver.

The targeting to the liver results in decreasing the amount of the protein to be shifted to the lung or the like, making it possible also to decrease the side effect by rhIL-2 in organs other than the target organ.

And it has been considered that in order to effectively exhibit the pharmaceutical effect of the physiologically active protein having such a liver accumulation property upon increasing the activity of the liver sinusoidal lymphocytes without incorporating the same into hepatocytes, this physiologically active protein has to be modified directly while maintaining the activity of the physiologically active protein as much as possible without formulating the physiologically active protein into preparations using a liposome or the like.

For example, attention has been drawn to the fact that if it is possible that rhIL-2 is site-specifically modified with a branched synthetic ligand such as Gal or GalNAc while maintaining the activity of rhIL-2 and is accumulated around hepatocytes without being incorporated into hepatocytes, it is bound to the IL-2 receptor (IL-2R) on liver sinusoidal lymphocytes as target cells whereby the activity is enhanced and antitumor effects to metastatic and primary liver cancers are expected.

However, the knowledges over the liver accumulation of the protein modified with such a branched ligand and the development of the activity thereof in the liver have not yet been obtained. Needless to say, the knowledge over the decrease in the side effect in organs other than the target organ has not yet been obtained at all.

DISCLOSURE OF THE INVENTION

The present inventors have found that recombinant human interleukin-2 (rhIL-2) site-specifically modified with a branched Gal ligand having an acidic or basic amino acid structure using a transglutaminase (B-TG) derived from microorganisms retains a biological activity compared to unmodified one, exhibits a liver accumulation property, is hardly incorporated into hepatocytes, and further minimizes remarkably the tumor in the mouse liver tumor model. Likewise, it has been found that human interferon-αmodified with a branched Gal ligand retains a biological activity compared to unmodified one, and exhibits a liver accumulation property.

It has been further found that an IL-2 fusion protein obtained by introducing one molecule of the Gal ligand and one molecule of the polyethylene glycol derivative site-specifically using two types of transglutaminases exhibits a higher liver accumulation property.

The present invention has been completed on the basis of such findings.

That is, it is an object of the present invention to provide a modified physiologically active protein which is obtained by modifying a protein that is expected to exhibit a physiological activity in the liver with a synthetic ligand upon using a lower binding affinity of the synthetic ligand for ASGR than that of a natural sugar chain for ASGR, whereby the physiologically active protein is selectively accumulated in the liver, target cells to the physiologically active protein present in the liver are activated, or active oxygen formed is removed to increase the antitumor effect, the antiviral effect and the anti-inflammatory effect, and the amount of the modified physiologically active protein delivered into the blood and other organs is decreased to reduce the side effect, as well as a pharmaceutical composition containing the same and having the excellent liver accumulation property.

Another object of the present invention is to provide a pharmaceutical composition containing the above-mentioned modified physiologically active protein and a pharmaceutically acceptable carrier, this composition having a liver accumulation property and reducing a side effect.

Still another object of the present invention is to provide a process for producing a modified physiologically active protein by modifying site-specifically a physiologically active protein using a transglutaminase derived from microorganisms.

The present invention relates to a pharmaceutical composition having a liver accumulation property, comprising a modified physiologically active protein which can be produced by reacting a physiologically active protein containing at least one Gln residue that becomes a substrate for a transglutaminase and having a molecular weight of from $1 \times 10^3$ to $2 \times 10^5$ with a branched-chain ligand composed of an amino acid derivative containing an amino group and a galactose (Gal) group or an N-acetylgalactosamine (GalNAc) group that become substrates for a transglutaminase, the branched-chain ligand having a lower binding affinity for an asialoglycoprotein receptor present on a surface of a hepatocyte than an asialoorosomucoid, in the presence of a transglutaminase derived from microorganisms to form an amide bond between the γ-carboxyamide group of the glutamine residue in the physiologically active protein and the terminal amino group in the branched-chain ligand; and a pharmaceutically acceptable carrier.

Further, the present invention relates to a modified physiologically active protein which has a liver accumulation property that its binding affinity for and asialoglycoprotein receptor present on a surface of a hepatocyte is lower than that of an asialoorosomucoid, and which can be produced by reacting a physiologically active protein containing at least one Gln residue that becomes a substrate for a transglutaminase and having a molecular weight of from $1 \times 10^3$ to $2 \times 10^5$ with a branched-chain ligand composed of an amino acid derivative containing an amino group and a galactose (Gal) group or an N-acetylgalactosamine (GalNAc) group that become substrates for a transglutaminase, the branched-chain ligand having a lower binding affinity for an asialoglycoprotein receptor present on a surface of a hepatocyte than an asialoorosomucoid, in the presence of a transglutaminase derived from microorganisms to form an amide bond between the γ-carboxyamide group of the glutamine residue in the physiologically active protein and the terminal amino group in the branched-chain ligand.

Still further, the present invention relates to a process for producing the modified physiologically active protein, which comprises reacting a physiologically active protein containing at least one Gln residue that becomes a substrate of a transglutaminase and having a molecular weight of from $1 \times 10^3$ to $2 \times 10^5$ with a branched-chain ligand composed of an amino acid derivative containing an amino group and a galactose (Gal) group or an N-acetylgalactosamine (GalNAc) group that become substrates of a transglutaminase, the branched-chain ligand having a lower binding affinity for an asialoglycoprotein receptor present on a surface of a hepatocyte than an asialoorosomucoid, in the presence of a transglutaminase derived from microorganisms to form an amide bond between the γ-carboxyamide group of the glutamine residue in the physiologically active protein and the terminal amino group in the branched-chain ligand.

BRIEF DESCRIPTION OF THE DRAWINGS

FIG. 11 is a table showing the results of the side effect by $(Gal)_3$-rhIL-2 (measuring the weight of the organ).

FIG. 12 is a table showing the results of the side effect of $(Gal)_3$-rhIL-2 (blood biochemical test).

BEST MODE OF CARRYING OUT THE INVENTION

Figure 1:
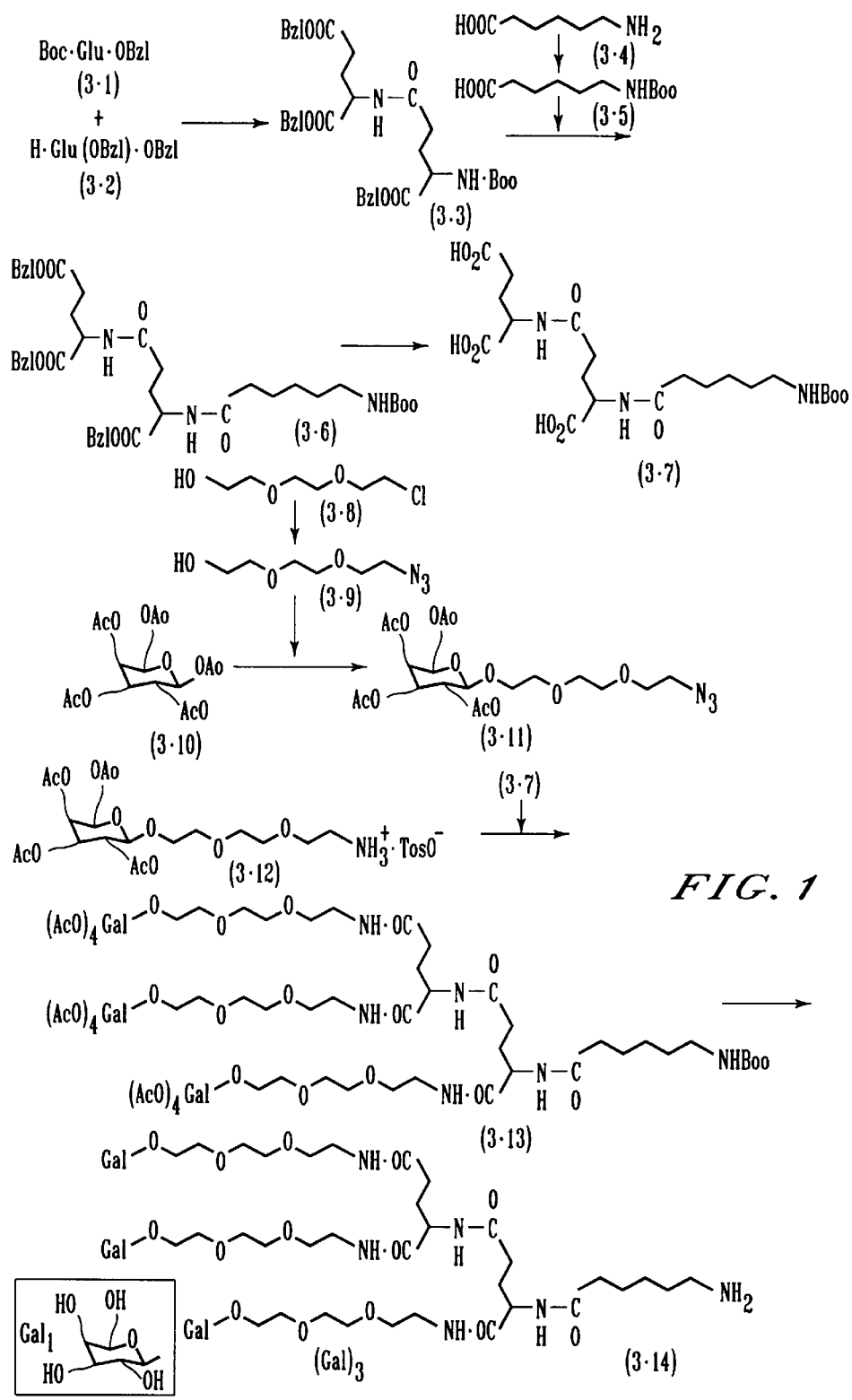
FIG. 1 is a flow chart of synthesizing $(Gal)_3$.

The present invention is described in detail below.

In the present invention, the physiologically active protein containing at least one Gln residue that becomes a substrate for a transglutaminase and having a molecular weight of from $1 \times 10^3$ to $2 \times 10^5$, preferably from $2 \times 10^3$ to $2 \times 10^5$, more preferably from $5 \times 10^3$ to $2 \times 10^5$, is a protein which increases the activity and reduces the side effect by being accumulated in the liver. Preferably, this physiologically active protein is not particularly limited if it has in a molecule at least one glutamine residue that becomes a substrate for a transglutaminase derived from microorganisms. Examples of the physiologically active proteins in the present invention include hepatocyte growth regulation factors such as a hepatocyte growth factor (HGF); cytokines such as interleukin-2 (IL-2), interleukin-12 (L-12), interferon-α, interferon-β and tumor necrosis factor (TNF); and antioxidases such as superoxide dismutase (SOD). Especially, interleukin-2 (IL-2) and interferons are preferable because they are expected to be accumulated in the liver.

These physiologically active proteins may be derived from animals, plants or microorganisms. Further, proteins produced by incorporating genes of these proteins into *Escherichia coli*, yeasts, Chinese hamster ovary cells or the like are also available. Still further, it is advisable to purify well the physiologically active protein of the present invention before use in order to minimize the influence by co-existent proteins.

The physiologically active protein of the present invention has preferably at least one Gln residue that becomes a substrate for a transglutaminase, preferably a transglutaminase derived from microorganisms in a molecule. Whether the Gln residue in the molecule of the physiologically active protein can become a substrate for a transglutaminase derived from microorganisms can be examined according to the method of Sato et al. (PCT/JP 95/00298) in which introduction of MDC as a fluorescent agent is identified.

When such a Gln residue is absent in the molecule of the physiologically active protein, it is also possible to introduce the Gln residue that becomes a substrate for a transglutaminase derived from microorganisms into the physiologically active protein by binding a peptide having at lest one Gln residue that becomes the substrate for the transglutaminase derived from microorganisms to the C-terminus or the N-terminus of the physiologically active protein. At this time, the peptide is one composed of from 3 to 20 amino acids and containing at least one Gln residue. Specific examples of such a peptide include those having the following amino acid sequences represented by one-character nomenclature of an amino acid.

P-K-P-Q-Q-F-M, (SEQ ID NO:1)
R-P-K-P-Q-Q-F-G-L (SEQ ID NO:2), and
R-P-K-P-Q-Q-F-M. (SEQ ID NO:3)

The peptide containing the Gln residue that becomes a substrate for a transglutaminase derived from microorganisms can be introduced into the physiologically active protein by the method of Sato, et al (WO 96/06181).

Even when the physiologically active protein contains a Gln residue that becomes a substrate for a transglutaminase derived from microorganisms in the molecule (like IL-2), the above-mentioned peptide can further be bound thereto. In this case, the transglutaminase derived from microorganisms is selectively reacted with the Gln residue in the molecule, and the physiologically active protein can be modified with two or more different ligands by reacting the Gln residue of the peptide with a transglutaminase of a different substrate specificity other than the transglutaminase derived from microorganisms, for example, a transglutaminase derived from animals.

With respect to IL-2, for example, it is possible that a peptide having an amino acid sequence such as P-K-P-Q-Q-F-M is bound to the N-terminus of IL-2, and a ligand such as a polyethylene glycol alkylamine is introduced into the Gln residue of the peptide using a transglutaminase derived from animals. Then, the branched-chain ligand of the present invention is selectively introduced into the amino acid sequence of IL-2 using a transglutaminase derived from microorganisms.

It is also one of the findings of the present invention that a desired ligand can selectively be introduced into the Gln residue alone in the specific position of the molecule upon using a transglutaminase derived from microorganisms.

The branched-chain ligand used in the present invention is a ligand of which the binding affinity for ASGR present on the surface of the hepatocyte is lower than that of ASOR, more preferably, a ligand by which the modified protein is not incorporated into cells in the incorporation test using mouse-separated hepatocytes. That is, it is a ligand containing a di-branched or tri-branched galactose or N-acetylgalactosamine formed on the basis of a branched sugar-chain structure having in the end galactose of an asialofetuin or ASOR sugar chain. Examples of the structure for branching include acidic or basic amino acids such as glutamic acid, aspartic acid and lysine, and tris (hydroxymethyl)aminomethane. Further, since the structure becomes a substrate for a transglutaminase, it has an alkylamine group in the end.

More specifically, the branched-chain ligand composed of the amino acid derivative having the amino group and the galactose (Gal) group or the N-acetylgalactosamine (GalNAc) group that become the substrates for the transglutaminase in the present invention is preferably an amino acid derivative having branched Gal or GalNAc, represented by formula (I)

Z—AA—W (I)

wherein

AA represents one or two basic or acidic amino acids in which Z or W may be an N-terminus, and when AA is two amino acids, they may have an amide bond in the α-position or the other position, W is an alkylamine derivative represented by the formula —$X^1$—$(CH_2)_n NH_2$ in which n is an integer of from 1 to 8, $X^1$ represents —CO— when W is bound to an amino group of an amino acid represented by AA, and represents —NH— when W is bound to a carboxyl group of an amino acid represented by AA, and Z is a galactose (Gal) or N-acetylgalactosamine (GalNAc)-containing group represented by the formula —$X^2$—$(CH_2CH_2O)_p$—R or the formula —$X^2$—$(CH_2)_q$—OR in which R represents Gal or GalNAc, p is an integer of from 1 to 6, q is an integer of from 1 to 18, $X^2$ represents —CO— when Z is bound to an amino group of an amino acid represented by AA, and represents —NH— when Z is bound to a carboxyl group of an amino acid represented by AA.

The group AA of the branched-chain ligand represented by formula (I) is preferably one derived from one or two glutamic acids or aspartic acids which are the same or different.

More specifically, examples of the branched-chain ligand in the present invention include compounds represented by formulas (II) to (XV).

(II)

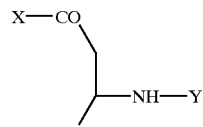
(III)

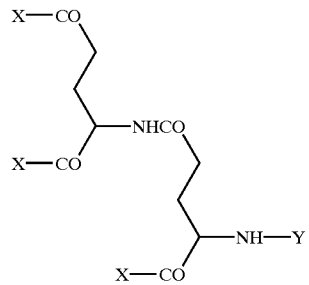
(IV)

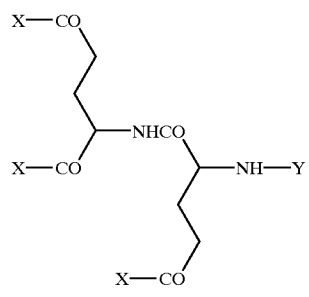
(V)

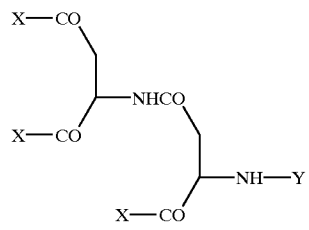
(VI)

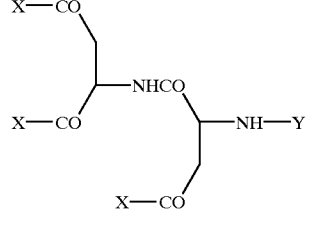
(VII)

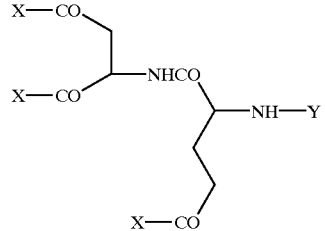
(VIII)

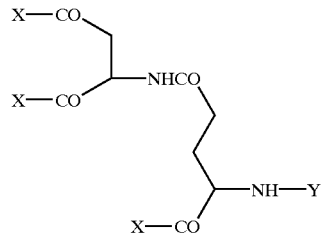
(IX)

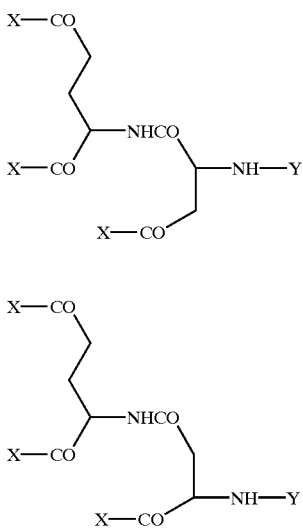

(X)

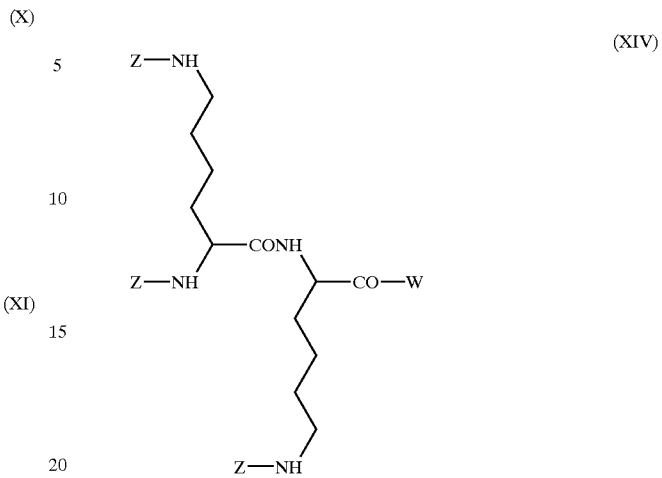

(XIV)

(XI)

wherein

X represents R—(OCH$_2$CH$_2$)$_p$—NH— or R—O(CH$_2$)$_q$—NH— in which R represents galactose or N-acetylgalactosamine, p is an integer of from 1 to 6, and q is an integer of from 1 to 18, Y represents —CO(CH$_2$)$_n$NH$_2$ in which n is an integer of om 1 to 8.

wherein

Z represents R(OCH$_2$CH$_2$)$_p$CO— or R—O(CH$_2$)$_q$CO— in which R represents galactose or N-acetylgalactosamine, p is an integer of from 1 to 6, and q is an integer of from 1 to 18, and W represents —NH(CH$_2$)$_n$NH$_2$ in which n is an integer of from 1 to 8.

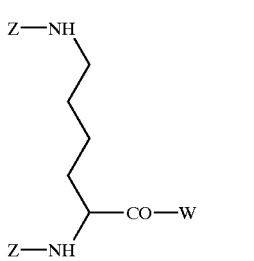

(XII)

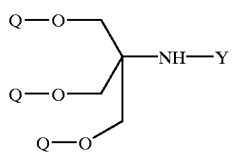

(XV)

(XIII)

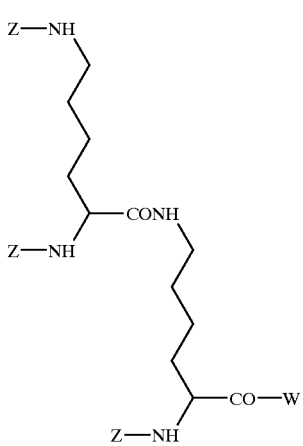

wherein

Q represents R(OCH$_2$CH$_2$)$_p$— or R—O(CH$_2$)$_q$— in which R represents galactose or N-acetylgalactosamine, p is an integer of from 1 to 6, and q is an integer of from 1 to 18, and Y represents —CO(CH$_2$)$_n$NH$_2$ in which n is an integer of from 1 to 8.

The above-mentioned compounds can be used as the branched-chain ligand of the present invention depending on the purpose and the type of the physiologically active protein. The tri-antenna type ligand of formula (IV) is preferable. Specifically, a ligand represented by formula (XVI)

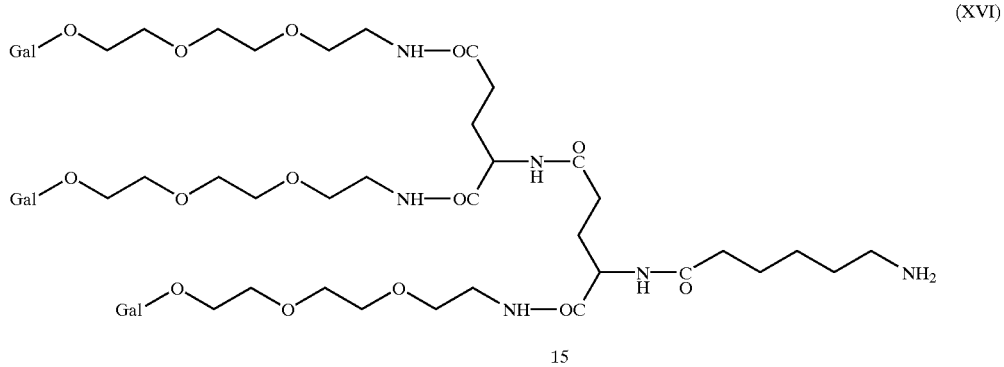

(XVI)

wherein Gal represents galactose or a ligand represented by formula (XVII)

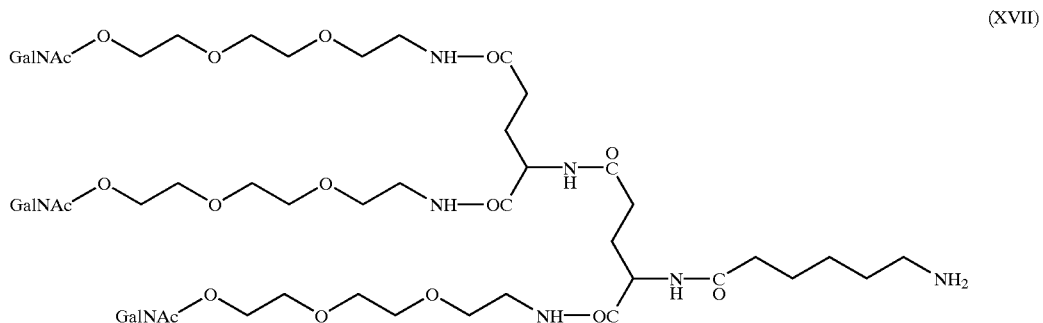

(XVII)

wherein GalNAc represents N-acetylgalactosamine (hereinafter referred to also as "(GalNAc)₃") is more preferable. The ligand (Gal)₃ represented by formula (XVI) is a ligand indicated by Compound (3–14) in FIG. 1, and the ligand (GalNAc)₃ represented by formula (XVII) is a ligand indicated by Compound (14) in FIG. 3.

The branched-chain ligand of the present invention can be produced by a usual method of an organic chemistry. Usually, derivatives of an alkyl group containing an amino group protected with a protective-group ordinarily used in a peptide chemistry, such as a butoxycarbonyl group are reacted with a mono- or di-amino acid to form alkylamine derivatives containing a protected mono- or di-amino acid, and a group containing a Gal group or a GalNAc group is then introduced therein, after which the protective group is eliminated. Thus, the desired ligand can be formed. In the above-mentioned reaction, the order of introducing the alkylamine group and the group containing the Gal group or the GalNAc group can be inverted.

More specifically, the branched-chain ligands of formulas (II) to (XI) can be formed by the following method, for example. That is, according to the method described in Japanese Patent Publication No. 202,085/1993, a branched structure having an N-Boc-alkylamine bound thereto is formed using glutamic acid or aspartic acid. Then, the carboxyl group thereof is reacted with an amino group of a triethylene glycol amine derivative containing an acetyl-protected hydroxyl group of the sugar under dehydro-condensation conditions, specifically, in a solvent that does not participate in the reaction (for example, acetonitrile, dimethylformamide, methylene chloride or ethylene chloride) in the presence of an appropriate catalyst (for example, N-hydroxysuccinimide or N,N'-dicyclohexylcarbodiimide) at a reaction temperature of from 0° C. to room temperature for from 1 to 24 hours, and then the deprotection is conducted to obtain the branched-chain ligand.

With respect to the synthesis of the compounds represented by formulas (XII) to (XIV), an alkylamine-bound branched structure can be formed using lysine according to the method of Haesler et al (Bioconjugate Chem., (1993), 4, 85–93).

With respect to the synthesis of the compound represented by formula (XV), an alkylamine-bound branched structure can be formed using tris(hydroxymethyl)aminomethane according to the method of Biessen, et al (J. Med. Chem., (1995), 38, 1538–1546).

The ligand represented by formula (XVI) can be produced according to the above-mentioned methods (refer to FIG. 1). Further, (GalNAc)₃ represented by formula (XVII) can also be produced according to these methods. It can be produced efficiently by the following methods (refer to FIG. 3).

First, galactosamine or its salt is acetylated to obtain N-acetylgalactosamine having a hydroxyl group protected with a protective group. Then, this compound is subjected to ring closure in the presence of a condensation agent such as trimethylsilyl trifluoromethanesulfonate or the like to form a compound represented by formula (XVIII)

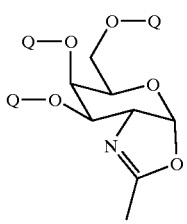

(XVIII)

wherein Q represents a hydrogen atom or a protective group of a hydroxyl group.

Figure 3A:
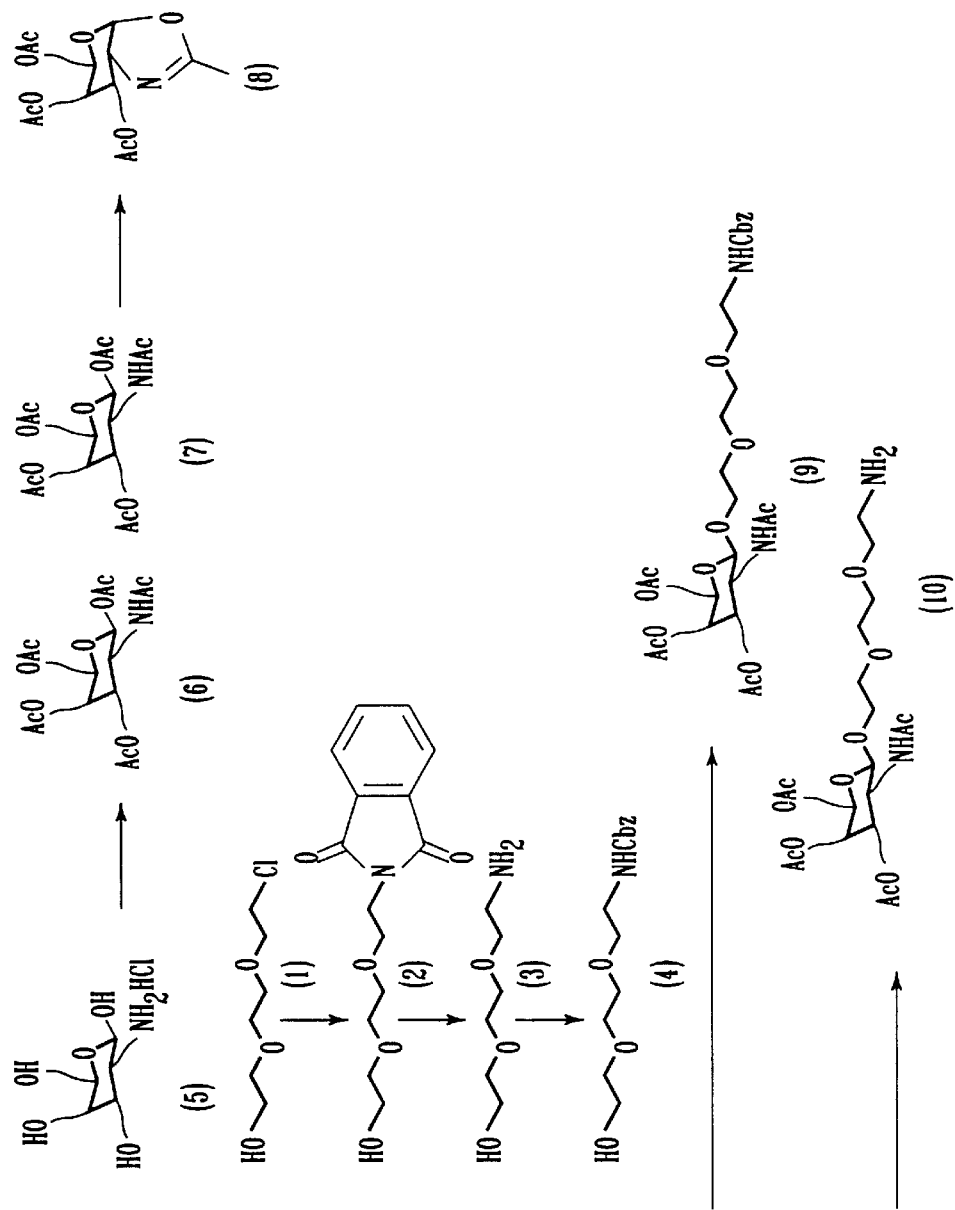
FIG. 3 is a flow chart of synthesizing $(GalNAc)_3$.
Figure 3B:
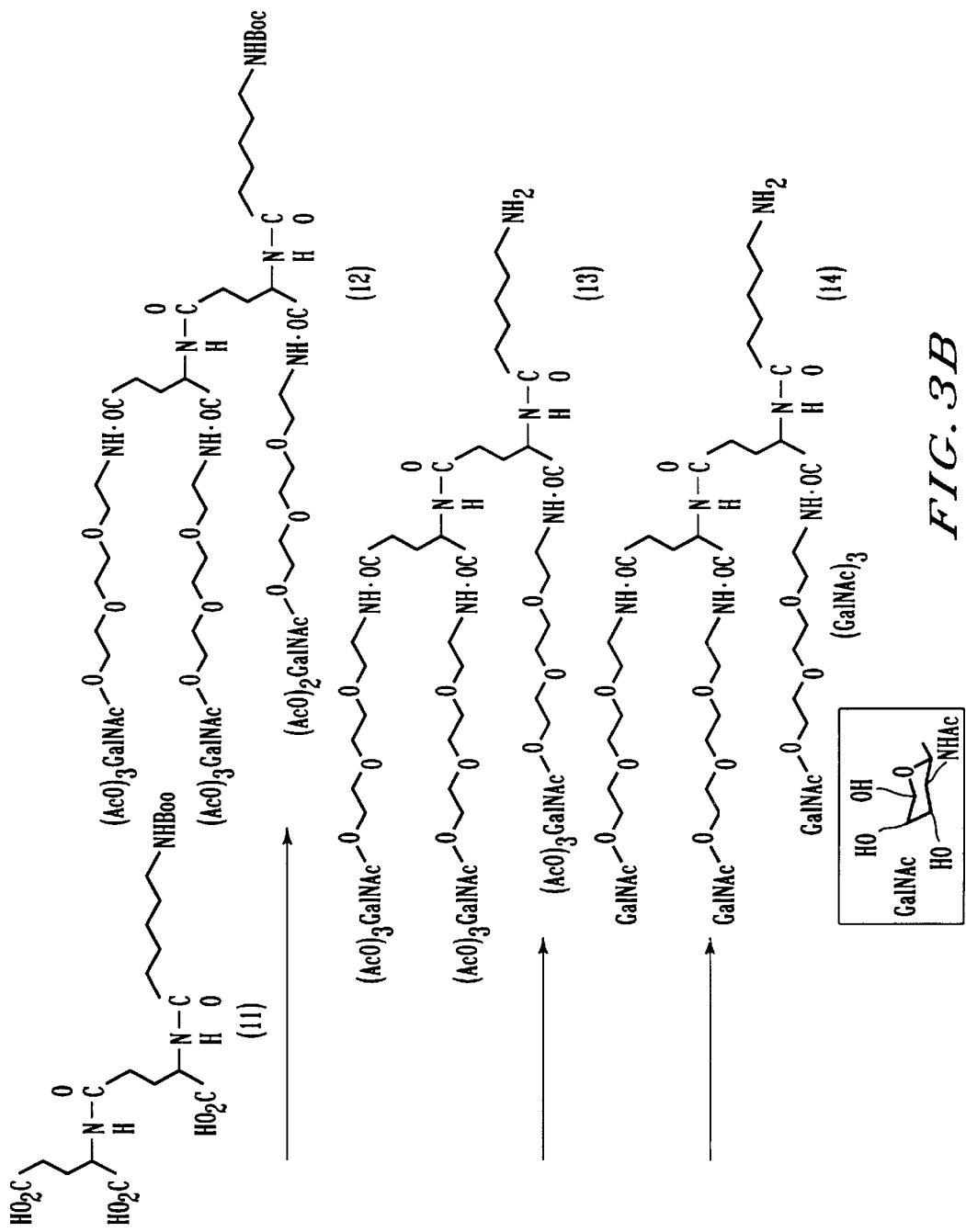

The compound represented by this formula (XVIII) in which the protective group is an acetyl group is shown as Compound (8) in FIG. 3.

Meanwhile, 2-[2-(2-chloroethoxy)ethoxy]ethanol (Compound (1) in FIG. 3) is aminated using a metal imide such as potassium phthalimide, and the resulting amino group is protected with a protective group such as a benzyloxycarbonyl group or the like to produce a compound (Compound (4) in FIG. 3).

The resulting 2-[2-(2-aminoethoxy)ethoxy]ethanol with the amino group protected is reacted with the compound represented by formula (XVIII) in the presence of a condensation agent such as trimethylsilyl trifluoromethanesulfonate, and the protective group is then eliminated. As a result, a compound represented by formula (XIX)

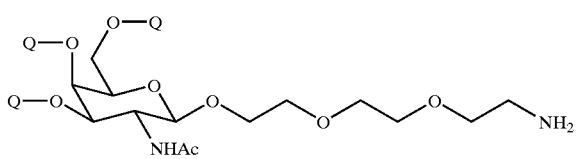

(XIX)

wherein Q represents a hydrogen atom or a protective group of a hydroxyl group can be produced. This compound represented by formula (XIX) in which the protective group of the hydroxyl group of N-acetylgalactosamine is an acetyl group is shown in FIG. 3 as Compound (10).

The resulting compound represented by formula (XIX) is condensed with a compound represented by formula (XX)

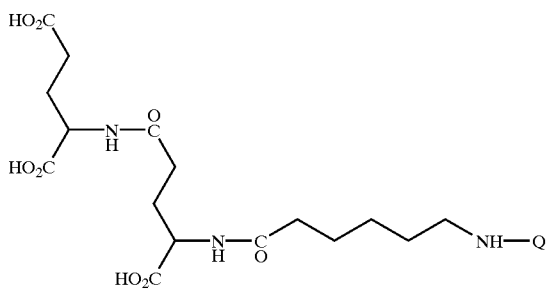

(XX)

wherein Q represents a hydrogen atom or a protective group of an amino group which can be formed using N-(tert-butoxycarbonyl)-L-glutamic acid-α-benzyl ester and L-glutamic acid-α,γ-dibenzyl ester p-toluenesulfonic acid salt as starting materials, in the presence of a condensation agent, and the protective group is eliminated as required, making it possible to produce a desired ligand represented by formula (XVII).

As the protective group of the hydroxyl group or the amino group indicated as the substituent Q, those used in the ordinary peptide chemistry can be used. An acetyl group, a tert-butoxycarbonyl group (Boc) and a benzyloxycarbonyl group (Cbz) are preferable.

Accordingly, the present invention is to provide a process for producing a ligand represented by formula (XVII) by the above-mentioned method.

These branched-chain ligands are reacted with the physiologically active protein in the presence of the transglutaminase (B-TG) derived from microorganisms according to the method of Takahara et al. (Japanese Laid-Open (Kokai) No. 89,278/1996) or the method of Sato et al. (WO 96/06181). That is, the physiologically active protein, the synthetic ligand and the transglutaminase, preferably the transglutaminase derived from microorganisms are reacted in an aqueous solution, preferably with a pH of approximately 7.5 at room temperature for 12 hours. The concentration ratio of the physiologically active protein to the synthetic ligand is preferably between 1:100 and 1:2000. Further, the amount of the transglutaminase used is between 0.01 and 1 unit per nmol of the protein. Still further, the two-molecule modification with the synthetic ligand and also with the polyethylene glycol alkylamine derivatives improves the retention of the protein in the blood and the stability thereof and increases the amount of the protein accumulated in the liver. That is, two different substrates are site-specifically bound upon using two types of transglutaminases different in the substrate specificity, preferably the transglutaminase derived from microorganisms and the transglutaminase derived from the guinea pig liver.

The pharmaceutical composition of the present invention can be used as a malignant tumor treating agent, an antiviral agent, an antirheumatic, an antiallergic, an immunomodulator, a circulatory function improving agent, an endocrine function improving agent, an agent for treating diseases caused by abnormal development of a protein or an abnormal function thereof according to a physiologically active protein to be bound to a ligand.

The pharmaceutical composition of the present invention can be formulated into preparations such as an intravenous or intramuscular injection, a rectal administration agent, a hydrophobic suppository, a water-soluble suppository and the like. These preparations can be produced in a usual manner using, as required, an excipient, a filler, a binder, a wetting agent, a disintegrant, a surface active agent, a lubricant, a buffer, a preservative, a solubilizer, an antiseptic, an analgesic, a stabilizer and the like which are ordinarily used. Usable examples of the additives which are non-toxic include, for example, lactose, fructose, dextrose, starch, gelatin, magnesium carbonate, synthetic magnesium silicate, talc, magnesium stearate, methyl cellulose, carboxymethyl cellulose or its salt, gum arabic, polyethylene glycol, syrup, vaselin, glycerin, ethanol, propylene glycol, citric acid, sodium chloride, sodium sulfite and sodium phosphate.

Examples of the administration of the pharmaceutical composition in the present invention includes parenteral administrations such as intravenous administration, subcutaneous administration, intramuscular administration and mucosal administration. The intravenous administration is preferable. In order to maximize the efficiency of delivery to the liver, it is advisable that the dose of the pharmaceutical composition is lower than the saturated dose of the pharmaceutical composition bound to the asialoglucoprotein receptor present in the hepatocyte of the liver. The dose of the modified physiologically active protein in the present invention can be adjusted to lower than the dose of the conventional unmodified physiologically active protein (the former is at least approximately one-fourth of the latter).

The dose thereof not only varies depending on the physiologically active protein used, but also is it determined appropriately in consideration of the use and the age, the sex and the degree of the progression of diseases of the patients. The dose of the pharmaceutical composition of the present invention can be reduced to one-several times of that of the unmodified protein because of its liver accumulation property.

Further, the present invention is to provide a method of curing or preventing diseases of animals including humans, such as a malignant tumor, a viral infection, an allergic disease, an immunological disease, a circulatory organ disease, an endocrine disease and the like.

Still further, the present invention is to provide the use of the medication containing the modified physiologically active protein at a dose required for treatment or prevention, examples of the medication being a malignant tumor treating agent, an antiviral agent, an antirheumatic, an antiallergic, an immunomodulator, a circulatory function improving agent, an endocrine function treating agent and the like.

EXAMPLES

The present invention is illustrated more specifically by referring to the following Examples. However, the present invention is not limited thereto.

Example 1

Production of (Gal)$_3$-rhIL-2

An rhIL-2 solution (39 ml) dissolved in a 50-mM acetate buffer (pH 5.0) containing 0.25-M NaCl was applied to a Sephadex G-25 column (supplied by Pharmacia) which had been equilibrated with a 200-mM Tris-hydrochloride buffer (pH 7.5), and was eluted with the above-mentioned buffer. The elute was monitored at an absorbance of 280 nm to obtain a protein elute fraction (48 ml). The protein of this elute fraction was adjusted to a concentration of 5 $\mu$M (330 ml).

To this elute fraction was added a branched Gal ligand ((Gal)$_3$, 472 mg) formed according to the method of Sato et al. (PCT/JP/95/00298) as shown in FIG. 1.

To this reaction solution were added 60 U of a transglutaminase derived from microorganisms, and the mixture was incubated overnight at room temperature.

The reaction solution was preliminarily treated with a "Sep-Pak C8 Cartridge" (supplied by Waters), and then purified several times through reversed-phase HPLC using a "YMC-Pack C8-AP" column (4.6×250 mm, supplied by Yamamura Kagaku K.K.) to remove the unreacted rhIL-2 fraction and (Gal)$_3$.

The purity of the purified product was measured through SDS-PAGE (using a "Homogenious 20" gel) using a "Phast system" (supplied by Pharmacia). As a result, with respect to the (Gal)$_3$-modified product ((Gal)$_3$-rhIL-2), the protein-derived band was identified only in the position where the molecular weight was increased by approximately 2 KDa presumably because one molecule of (Gal)$_3$ was bound to the unmodified product.

The amount of the modified product was 5.3 mg (yield 21%). A part of this fraction was sampled, and then applied to a Sephadex G-25 column which had been equilibrated with PBS (−) (pH 7.5), and eluted with the above-mentioned buffer to give the protein fraction (amount 3.1 mg).

Example 2

Production of PEG12, (Gal)$_3$-rX2-IL-2

(1) Production of PEG12-rX2-IL-2

A 5-milliliter solution of rX2-IL-2 (fusion protein obtained by adding a P-K-P-Q-Q-F-M amino acid sequence to the N-terminus of hIL-2) prepared by the method of Sato et al. (PCT/JP/95/00298) was applied to a Sephadex G-25 column (supplied by Pharmacia) which had been equilibrated with a 100-mM Tris-hydrochloride buffer (containing 10-mM CaCl$_2$, pH 7.5), and was eluted with the above-mentioned buffer. The elute was monitored at an absorbance of 280 nm to obtain a protein elute fraction (6 ml). The protein of this elute fraction was adjusted to a concentration of 25 $\mu$M/ml (10 ml).

Figure 2:
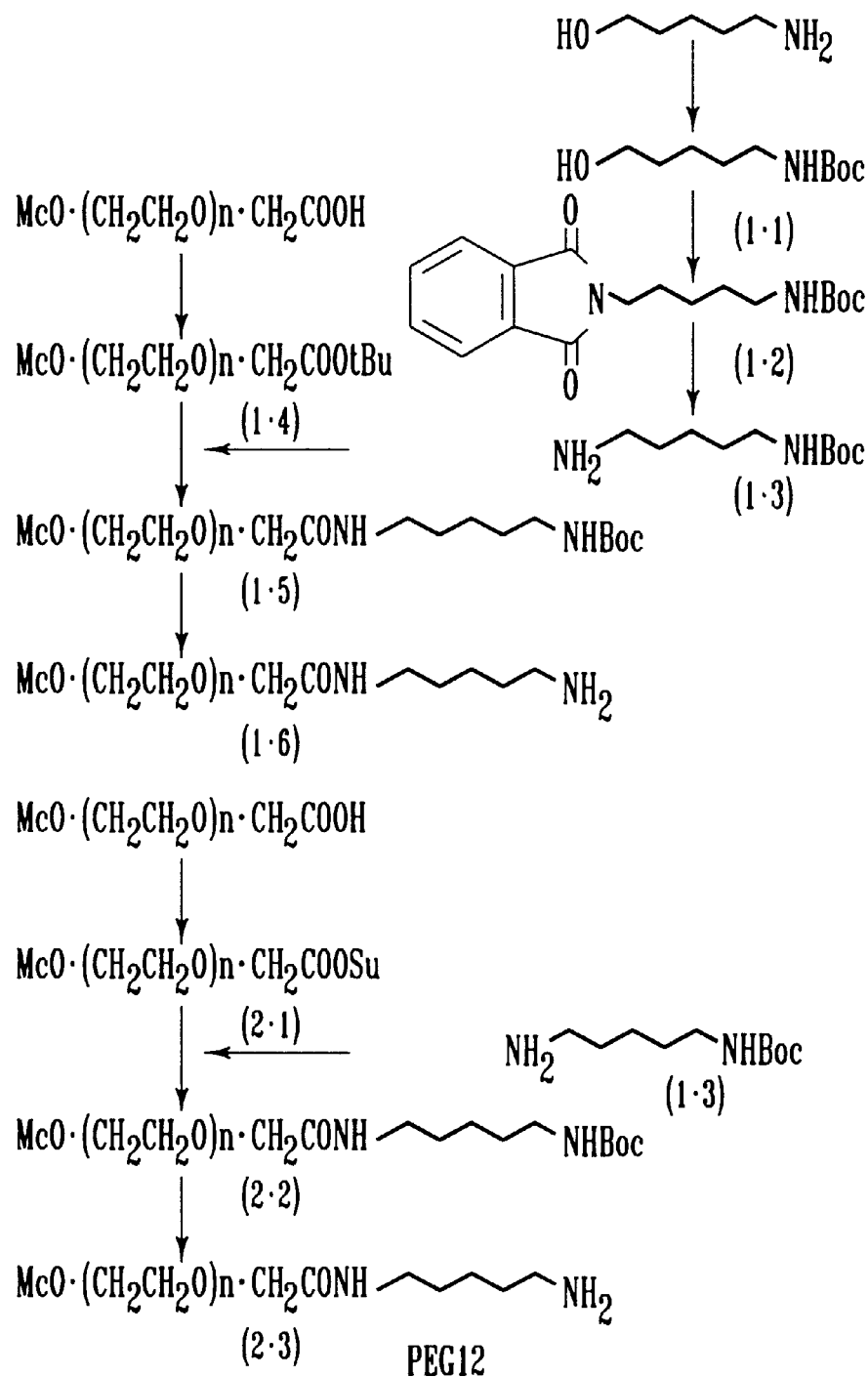
FIG. 2 is a flow chart of synthesizing PEG12.

To this elute fraction was added polyethylene glycol alkylamine (formula (2–3) in FIG. 2, PEG12, average molecular weight 12 KDa, 750 mg) prepared by the method of Sato et al. (PCT/JP/95/002980) as shown in FIG. 2.

To this reaction solution were added 2 U of a transglutaminase derived from the guinea pig liver (supplied by Sigma), and the mixture was incubated overnight at room temperature.

The reaction solution was preliminarily treated with a "Sep-Pak C8 Cartridge" (supplied by Waters), and then purified several times through reversed-phase HPLC using a "YMC-Pack C8-AP" column (4.6×250 mm, supplied by Yamamura Kagaku K.K.) to remove the unreacted rX2-IL-2 fraction and PEG12.

The purity of the purified product was measured through SDS-PAGE (using a "Homogenious 20" gel) using a "Phast system" (supplied by Pharmacia). As a result, with respect to the PEG12-modified product (PEG12-rX2-IL-2), the protein-derived band was identified only in the position where the molecular weight was increased by approximately 20 KDa presumably because one molecule of PEG12 was bound to the unmodified product. The amount of the modified product was 0.484 mg (yield 2%).

(2) Production of PEG12, (Gal)$_3$-rX2-IL-2

The above-mentioned PEG12-rX2-IL-2 solution was applied to a Sephadex G-25 column (supplied by Pharmacia) which had been equilibrated with a 200-mM Tris-hydrochloride buffer (pH 7.5), and was eluted with the above-mentioned buffer. The elute was monitored at an absorbance of 280 nm to obtain a protein elute fraction (3 ml). The protein of this elute fraction was adjusted to a concentration of 5 $\mu$M/ml (3 ml). A galactose ligand ((Gal)$_3$, 17 mg) formed according to the method of Sato et al. (PCT/JP/95/00298) was added thereto. To this reaction solution were added 15 U of a transglutaminase derived from microorganisms, and the mixture was incubated overnight at room temperature.

The reaction solution was preliminarily treated with a "Sep-Pak C8 Cartridge" (supplied by Waters), and then purified several times through reversed-phase HPLC using a "YMC-Pack C8-AP" column (4.6×250 mm, supplied by Yamamura Kagaku K.K.) to remove the unreacted PEG12-rX2-IL2 fraction and (Gal)$_3$.

The purity of the purified product was measured through SDS-PAGE (using a "Homogenious 20" gel) using a "Phast system" (supplied by Pharmacia). As a result, with respect to the product modified with PEG12 and (Gal)$_3$ (PEG12, (Gal)₃-rX2-IL-2), the protein-derived band was identified only in the position where the molecular weight was increased by approximately 2 KDa presumably because one molecule of (Gal)₃ was bound to PEG12-rX2-IL-2. The amount of the modified product was 0.05 mg (yield 1%).

Example 3

Synthesis of ((GalNAc)₃ (refer to FIG. 3))

(1) Synthesis of Compound (4)

Synthesis of Compound (4) was conducted upon improving the method of Yamada et al. (Japanese Laid-Open (Kokai) No. 202,085/1993). Five-hundred grams (2.96 mols) of 2-[2-(2-chloroethoxy)ethoxy]ethanol (Compound (1)) were added to a mixed solution of 596 g (3.22 mols) of potassium phthalimide and DMF (3.5 liters), and the mixture was stirred in an oil bath (100° C.) for 17 hours while being heated. The reaction solution was cooled to room temperature, and an insoluble matter was filtered. The filtrate was concentrated under reduced pressure. The residue was extracted with methylene chloride (300 ml), and the solvent was distilled off to obtain 895.6 g of Compound (2) as a yellow oil (crude product).

The resulting crude product was dissolved in EtOH (14 liters), and 198 ml (3.27 mols) of 80-% hydrazine monohydrate were added thereto. Then, the mixture was heat-refluxed for 2 hours while being stirred with a mechanical stirrer. The reaction solution was cooled to room temperature, and an insoluble matter was then filtered. The filtrate was concentrated under reduced pressure. To the residue were added 3 liters of methylene chloride, and the mixture was stirred at room temperature for 30 minutes. Then, an insoluble matter was filtered. The filtrate was concentrated under reduced pressure to obtain 484 g of Compound (3) as a yellow oil (crude product).

The above-mentioned compound (3) (483.8 g) was dissolved in 5.4 liters of water, and the solution was cooled in an ice water bath. NaHCO₃ (273 g) and benzyloxycarbonyl chloride (33-% toluene solution, 1,550 ml) were alternately added thereto each five times while being stirred, and the mixture was stirred overnight at room temperature. The reaction solution was divided into layers, and the aqueous layer was extracted with ethyl acetate. The combined organic layer was washed with a saturated aqueous solution of sodium chloride, and then dried over anhydrous magnesium sulfate. The solvent was distilled off under reduced pressure, and the residue obtained was purified through silica gel column chromatography (silica gel=4 kg) using ethyl acetate as an eluent to obtain 393 g of the above-mentioned Compound (4) as a colorless oil.

(2) Synthesis of Compound (9)

The synthesis of Compound (9) which is a galactosamine derivative was conducted by the method of Japanese Laid-Open (Kokai) No. 202,085/1993.

That is, 150 g of galactosamine hydrochloride (Compound (5)) were dissolved in a mixed solvent of 2.8 liters of MeOH and 190 ml of triethylamine, and 1.25 liters of acetic anhydride were added thereto dropwise at room temperature. After the solution was stirred overnight at room temperature, the solvent was distilled off under reduced pressure. Subsequently, 1,500 ml of pyridine and 500 ml of acetic anhydride were added thereto, and the mixture was stirred overnight at room temperature. After the solvent was distilled off again under reduced pressure, the residue was formed into an ethyl acetate solution, washed with water, and further concentrated.

The crystals precipitated were collected through filtration, and the filtrate was concentrated. The residue was then purified through silica gel chromatography to obtain 89.4 g of an α,β-acetate (Compound (7), (6)) mixture) (2:1) (silica gel=4 kg, CHCl₃:MeOH=10:1).

Further, the mother liquor was concentrated to dryness, and the resulting product was then purified through silica gel column chromatography to obtain 23.9 g of an α-acetate (Compound (7)) (silica gel=4 kg, AcOEt).

The above-mentioned α,β-acetate (Compounds (7), (6)) mixture (2:1) (81.4 g) was dissolved in 1 liter of 1,2-dichloroethane (EDC), and 39.8 ml of trimethylsilyl trifluoromethanesulfonate (TMSOTf) were added thereto dropwise at room temperature. The mixture was reacted overnight at 40° C., and 2 equivalents of Et₃N were added thereto. Subsequently, the solvent was distilled off. Meanwhile, 23.9 g of the above-mentioned α-acetate (Compound (7)) were dissolved in 300 ml of 1,2-dichloroethane (EDC), and 11.7 ml of TMSOTf were added thereto dropwise at room temperature. After the reaction was conducted at 40° C. for 3 hours, 2 equivalents of Et₃N were added thereto, and the solvent was then distilled off. The residue was collected, and purified through silica gel chromatography to obtain 83.6 g of Compound (8) (silica gel=4 kg, CHCl₃:MeOH=20:1).

The above-mentioned compound (8) (83.0 g) and 142.8 g of Compound (4) which had been synthesized were dissolved in 1 liter of 1,2-dichloromethane, and 53.2 ml of TMSOTf were added thereto dropwise at 50° C. in the presence of MS4A (molecular sieves 4A). The mixture was reacted overnight at room temperature while being stirred. Then, 1 liter of water was added thereto, and the mixture was extracted with 2 liters of chloroform. The extract was washed with water and with a saturated aqueous solution of sodium chloride, then dried over anhydrous sodium sulfate. Thereafter, the solvent was distilled off under reduced pressure. The residue was purified twice through silica gel column chromatography to obtain 145 g of the above-mentioned compound (Compound (9)) (silica gel=4 kg, AcOEt→CHCl₃:MeOH=20:1 to 10:1).

(3) Synthesis of Compound (14) ((GalNAc)₃)

The above-mentioned Compound (9) (71.1 g) was dissolved in 1.5 liters of EtOH, and 22.8 g of p-toluenesulfonic acid monohydrate were added thereto. The mixture was stirred overnight at room temperature in the presence of 22.6 g of 5-% Pd/C in a hydrogen atmosphere. The reaction solution was filtered using a Celite, and then concentrated to dryness under reduced pressure. The residue was dissolved in 500 ml of acetonitrile, and concentrated to dryness, and this procedure was repeated four times. The residue was dissolved in 200 ml of acetonitrile, and 13.3 ml of N-methylmorpholine were added thereto to prepare a solution of Compound (10).

Meanwhile, a 100-milliliter DMF solution containing 19.3 g of Compound (11) which had been formed by the method of Sato et al. (PCT/JP95/00298 (WO 96/06181)) using N-(tert-butoxycarbonyl)-L-glutamic acid-α-benzyl ester and L-glutamic acid-α,γ-dibenzyl ester p-toluenesulfonic acid salt as starting materials was cooled in an ice water bath. N-hydroxysuccinic acid imide (13.7 g) and 4.63 g of DCC were added thereto, and the mixture was stirred for several minutes. To this reaction solution were added dropwise 200 ml of an acetonitrile solution containing 78 g of the above-mentioned Compound (10), and the mixture was stirred overnight while being cooled (15° C.). The insoluble matter was separated through filtration, and the solvent was distilled off under reduced pressure. The residue was purified through silica gel column chromatography to obtain 16.1 g of Compound (12) being an intermediate as a colorless solid (silica gel=4 kg, CHCl$_3$:MeOH= 20:1 to 10:1). The structure of Compound (12) was identified through FAB-MS (m/z (M+H)$^+$ 1870.9).

A methylene chloride (65 ml) solution containing 15.3 g of Compound (12) prepared was cooled in an ice water bath, and 65 ml of trifluoroacetic acid (TFA) were added thereto. Subsequently, the solution was stirred at room temperature for 1 hour. The solvent was distilled off under reduced pressure. In order to remove the residual TFA, the residue was dissolved in 50 ml of EtOH, and the solution was evaporated to dryness under reduced pressure. This procedure was repeated three times. Then, the residue was dissolved in 70 ml of methylene chloride. The mixture was neutralized with the addition of a 28-% NaOMe/MeOH solution while being cooled in an ice water bath. The solvent was distilled off under reduced pressure, and the residue was purified through silica gel column chromatography to obtain 11.2 g of Compound (13) being an intermediate (silica gel=460 g, CH$_2$Cl$_2$:MeOH=10:1 to 3:1). The structure of Compound (13) was identified through $^1$HNMR and electrospray ionization quadrupole mass spectrometry (ESI+ QIMS).

$^1$H NMR (600 MHz, CDCL$_3$): δ2.01 (s, Ac, 9H), 2.02 (s, Ac, 9H), 2.05 (s, Ac, 9H), 2.15 (s, Ac, 9H), 3.05–3.16 (br, —CH$_2$—NH$_2$, 2H)

ESI +QIMS: m/z (M+H)$^+$ 1770.4

The above-mentioned Compound (13) (6.64 g) was dissolved in 184 ml of MeOH, and 0.83 milliliters of a 28-% NaOMe/MeOH solution were added thereto while being cooled in an ice water bath. The mixture was stirred at room temperature for 5 hours, and the reaction solution was then cooled in an ice water bath, and neutralized with the addition of Dowex 50W which had been washed well with MeOH. The resin was separated through filtration, and the solvent was then distilled off under reduced pressure. The residue was dried overnight at 50° C. under reduced pressure to obtain 3.4 g of (GalNAc)$_3$ (Compound (14)).

$^1$H NMR (600 MHz, D$_2$O): δ1.48–1.55 (m, 2H), 1.70–1.83 (m, 4H), 2.04–2.12 (m, 2H), 2.17 (s, 9H), 2.16–2.24 (m, 2H), 2.47 (t, 4H), 2.55 (t, 2H), 3.14 (t, 2H), 3.45–3.58 (m, 6H), 3.70–3.95 (m, 41H) 4.02–4.08 (m, 6H), 4.12–4.18 (br, 2H), 4.32–4.42 (m, 2H), 4.63 (d, 2H)

$^{13}$C NMR (150 MHz, D$_2$O): δ23.0, 25.4, 25.9, 27.2, 27.6, 27.9, 32.2, 32.6, 35.8, 39.7, 40.0, 49.6, 53.1, 54.0, 54.2, 61.7, 68.6, 69.5 69.6, 70.2, 70.4, 71.8, 75.9, 102.3, 174.3, 174.3, 175.4, 175.6, 176.6, 177.5

ESI+QIMS:m/z (M+H)$^+$ 1393.1

Example 4

Preparation of (GalNAc)$_3$-IL-2

An rhIL-2 solution (11 ml) dissolved in a 50 mM acetate buffer (pH 5.0) containing 0.25 M NaCl was applied to a Sephadex G-25 column (supplied by Pharmacia) which had been equilibrated with a 200 mM Tris-hydrochloride buffer (pH 7.5), and eluted with the same buffer. The elute was monitored at an absorbance of 280 nm to obtain an elute fraction of a protein (20 ml, 6.8 μM). The concentration of the protein of this elute fraction was adjusted to 5 μM (26 ml).

To 13 ml of this elute fraction were added 3.47 mg of the branched N-acetylgalactosamine ligand ((GalNAc)$_3$ formed by the method described in the above-mentioned Example 3. To the reaction solution were added approximately 32.5 U of a microorganism-derived transglutaminase, and the mixture was incubated overnight at room temperature.

The reaction solution was preliminarily treated with a "Sep-pak C8 Cartridge" (supplied by Wqaters), and then purified several times through reversed-phase HPLC using a "YMC-Pack C8-AP" column (4.6×250 mm, supplied by Yamamura Kagaku K.K.) to remove the unreacted IL-2 fraction and (GalNAc)$_3$.

The purity of the purified product was measured through SDS-PAGE using a "Phast system" (supplied by Pharmacia) (using a "Homogenious 20" gel). As a result, with respect to the product modified with (GalNAc)$_3$ ((GalNAc)$_3$-rhIL-2), the protein-derived band was identified only in the position where the molecular weight was increased by approximately 2 KDa presumably because one molecule of (GalNAc)$_3$ was bound to the unmodified product. The amount of the modified product was 401 μg (yield 40%).

A part of the fraction obtained was subjected to buffer exchange by repeatedly conducting the concentration using Molcut L (LGC, supplied by Millipore) which had been equilibrated with PBS (pH 7.4).

Example 5

Preparation of (Gal)$_3$-INF-α

Two-hundred micrograms of human INF-α(2b) freeze-dried were dissolved in 1,465 μl of a 200 mM Tris-hydrochloride buffer, and a branched galactose ligand ((Gal)$_3$, 6.5 mg) synthesized was added thereto. To this reaction solution were added approximately 0.7 U of a microorganism-derived transglutaminase, and the mixture was incubated at room temperature for 4 hours.

The reaction solution was purified several times through reversed-phase HPLC using a "YMC-Pack C8-AP" column (4.6×250 mm, supplied by Yamamura Kagaku K.K.) to remove the unreacted INF-α(2b) fraction and (Gal)$_3$. The fraction obtained was subjected to buffer exchange by repeatedly conducting the concentration using Molcut L (LGC, supplied by Millipore) which had been equilibrated with PBS (pH 7.4).

The purity of the purified product was measured through SDS-PAGE using a "Phast system" (supplied by Pharmacia) (using a "Homogenious 20" gel). As. a result, with respect to the product modified with (Gal)$_3$ ((Gal)$_3$-INF-α), the protein-derived band was identified only in the position where the molecular weight was increased by approximately 2 KDa presumably because one molecule of (Gal)$_3$ was bound to the unmodified product. The amount of the modified product was 50 μg (yield 75%).

Example 6

Preparation of (Gal)$_3$-Tyr-Boc, (GalNAc)$_3$-Tyr-Boc

Figure 4:
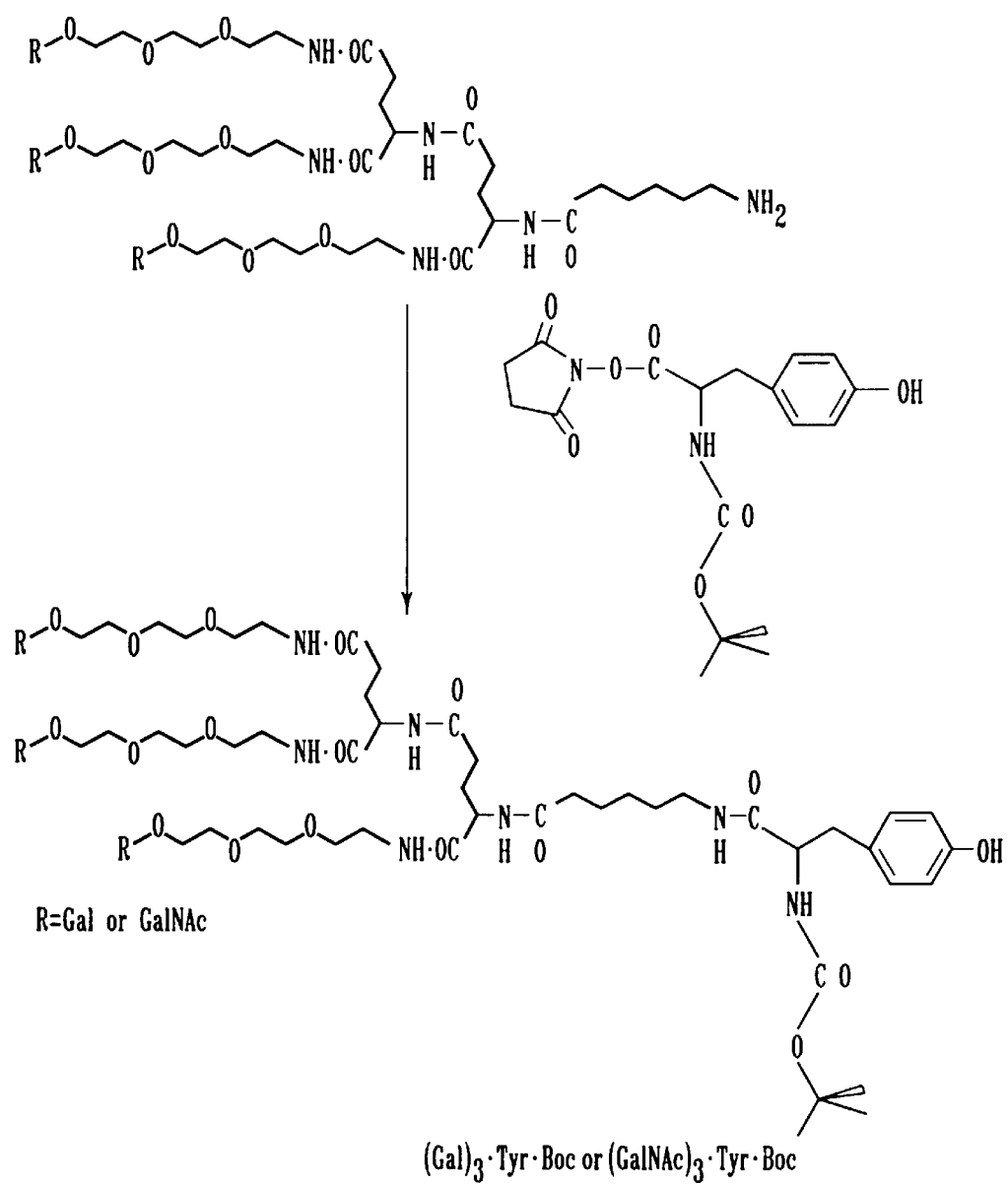
FIG. 4 is a flow chart of synthesizing $(Gal)_3$-Tyr-Boc and $(GalNAc)_3$-Tyr-Boc.

The synthesis of Tyr derivative for iodo-labeling was conducted by the method of Tamura et al. (T. Tamura et al., Anal. Biochem. 216, 335–344 (1994)) (refer to FIG. 4.). That is, 30 μmols of (Gal)$_3$ or (GalNAc)$_3$ were dissolved in 3.6 ml of dimethylformamide, and 1.13 g of Boc-Tyr-NTH (supplied by Sigma) were added thereto. The solution was stirred at 50° C. for 5 hours. After the reaction solution was cooled, 1 N NaOH was added thereto, and a precipitate was removed through centrifugation. The supernatant was added to a Sephadex G-25 column (supplied by Pharmacia) which had been equilibrated with 1% (w) of pyridine and acetic acid to obtain a Tyr-Boc derivative fraction monitored at 280 nm. The fraction obtained was freeze-dried, and then dissolved again in a 0.1% TFA solution. The solution was purified through reversed-phase HPLC using an "Inertsil ODS-2" column (4.6×150 mm, supplied by GL Science Inc.)

to form 14.7 mg of a Tyr-Boc derivative ((Gal)$_3$-Tyr-Boc) and 28.9 mg of a Tyr-Boc derivative ((GalNAc)$_3$-Tyr-Boc) having a peak purity of 90% or more. The structures of the products were identiried through electrospray ionization mass spectrometry (ESI-MS).

ESI-MS:

(Gal)$_3$-Tyr-Boc; m/z (M+H)$^+$ 1532.8, (GalNAc)$_3$-Tyr-Boc; m/z (M+H)$^+$ 1655.6

Example 7

Identification of the Modified Position

One hundred micrograms.(calculated as IL-2) of each of freeze-dried products of the fraction sampled through reversed-phase HPLC in the above-mentioned Example 1 and rhIL-2 were reductively carboxymethylated according to the method of Tsuji et al. (Biochemistry, (1987), 26, 3129–3134). Fifty micrograms of the freeze-dried powder of the reductively carboxymethylated product was dissolved in 50 microliters of an ammonium hydrogencarbonate buffer (pH 7.9), and the mixture was digested with the addition of 2 μg of "V8 protease", and then freeze-dried. Subsequently, 2 μg of "TPCK-trypsin" were dissolved in 50 microliters of a 50-mM ammonium hydrogencarbonate (pH 7.9) to conduct enzymolysis at 37° C. for 4 hours. The reaction solution was analyzed as such through LC/MS to prepare a peptide map for comparison. As a result, it was observed that a peak ascribable to the amino acid sequence containing Gln-74 in (Gal)$_3$-rhIL-2 disappeared. Consequently, it was identified that the branched-chain ligand (Gal)$_3$ of the present invention was bound to Gln-74 of rhIL-2 through B-TG position-selectively.

Example 8

IL-2 Activity of a Modified Product

The IL-2 biological activity of (Gal)$_3$-rhIL-2, (GalNAc)$_3$-rhIL-2, PEG12, (Gal)$_3$-rX2-IL-2 and rhIL-2 was measured by the method of Gills et al. (J. Immunol., 120, 2027 (1978)) using IL-2 dependent mouse cells "CTLL-2" (ATCC T1B 214) obtained from ATCC.

Consequently, the specific activity of (Gal)$_3$-rhIL-2 to rhIL-2 was 102%, and it proved that the modified product maintained the biological activity of IL-2. Further, the specific activity of (GalNAc)$_3$-rhIL-2 to rhIL-2 was 110%, and it proved that the (GalNAc)$_3$-modified product maintained the biological activity of IL-2. Further, the specific activity of PEG12, (Gal)$_3$-rX2-IL-2 to rX2-IL-2 was 126%, and it proved that the two-molecule-modified product maintained the biological activity of rX2-IL-2.

Example 9

Activity of Modified INF

Human IFN bioassay was conducted by the method of Watabe et al. (Lymphokines and Interferones; A Practical Approach, IRL Press, Oxford, 1987) based on inhibition of a cell denaturation effect by viruses using FL cells. That is, when a virus was used in an amount by which to induce 100% cell denaturation, cells was treated in advance with an IFN sample dilute solution. The IFN potency of the sample dilute solution given when the viral cell denaturation was inhibited by 50% was rated as 1 unit (IU). The IFN biological activities of (Gal)$_3$-INF-α and INF-α were calculated on the basis of the potency of the human INF-α standard product (supplied by The Green Cross Corporation).

Consequently, the biological activities of (Gal)$_3$-INF-α and INF-α were 1.17×10$^8$ IU/mg and 1.42×10$^8$ IU/mg respectively. As a result, the specific activity of (Gal)$_3$-INF-α to unmodified INF-α was 82%, and it proved that the modified product maintained the biological activity of INF-α(2b).

Example 10

Liver Accumulation Property of a Modified Product (Gal)$_3$-rhIL-2, (GalNAc)$_3$-rhIL-2, asialoorosomucoid [ASOR, produced by the method of Bider et al. (Eur. J. Biochem., (1995), 230, 207–212) using human orosomucoid (OR) or al-acid glycoprotein, supplied by Sigma] or rhIL-2 was intravenously administered into mice (C57BL/6, CRJ, 6W, male) at a dose of 3.2 nmols/kg. After fixed periods of time (2 minutes, 15 minutes, 30 minutes and 60 minutes), the blood was sampled, and the liver was extracted. The plasma was sampled in a usual manner, and the concentration of the specimen was measured through ELISA. The liver was homogenized with the addition of a 0.1% BSA-containing PBS (−) in a 9-fold amount, and centrifuged at 3,000 rpm for 5 minutes. Subsequently, the supernatant was diluted with an ELISA buffer (containing 0.05 M Tris HCl, 1 mM MgCl$_2$, 0.15 M NaCl, 0.05% (v/v), Tween 20, 0.02% (w/v) NaN$_3$ and 1% (w/v) BSA, pH 8.1), and the concentration in the liver was measured through ELISA.

ELISA of IL-2 was conducted using an anti-human IL-2 mouse monoclonal antibody (supplied by Boehringer Mannheim) as a primary antibody, an anti-human IL-2 rabbit polyclonal antibody as a secondary antibody and an alkali phosphatase-labeled anti-rabit IgG (γ+L) polyclonal antibody (goat) (supplied by Tago) as a tertiary antibody. On the other hand, ELISA of ASOR was conducted using a purified human α1-acid glycoprotein sheep polyclonal antibody (supplied by Binding Site) as a primary antibody, a purified anti-human α1-acid glycoprotein rabbit polyclonal antibody as a secondary antibody and an alkali phosphatase-labeled anti-rabbit IgG (γ+L) polyclonal antibody (goat) (supplied by Tago) as a tertiary antibody.

Figure 5A:
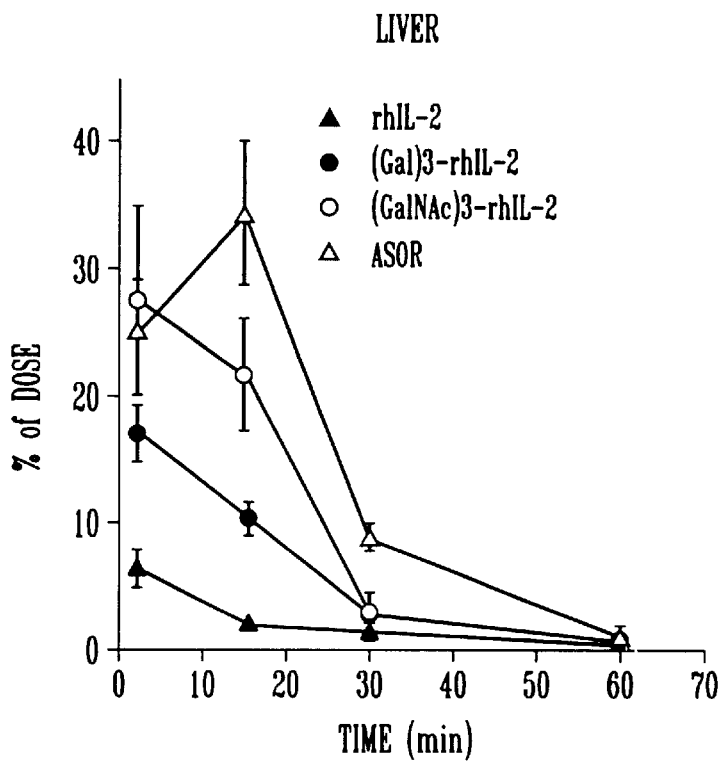
FIG. 5 is a graph showing a change in the amounts of $(Gal)_3$-rhIL-2, $(GalNac)_3$-rhIL-2 and ASOR in the plasma and the liver.
Figure 5B:
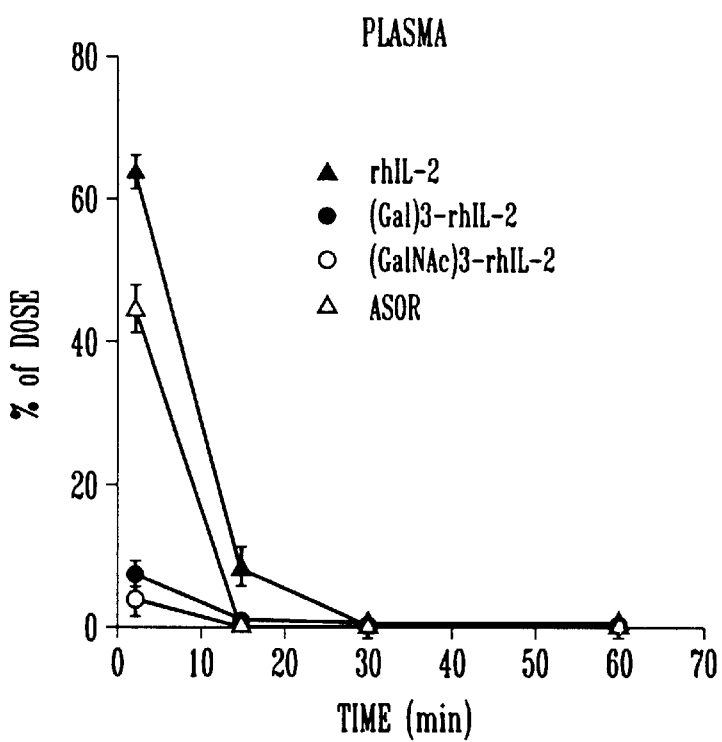

Consequently, as shown in FIG. 5, the concentrations of (Gal)$_3$-rhIL-2 and (GalNAc)$_3$-rhIL-2 in the plasma were changed at a lower level than that of rhIL-2. Meanwhile, the concentrations of (Gal)$_3$-rhIL-2 and (GalNAc)$_3$-rhIL-2 in the liver were changed at by far a higher level, and it proved that IL-2 could be accumulated in the liver by the modification with (Gal)$_3$ and (GalNAc)$_3$. AUCs (area under the concentration curve) of (Gal)$_3$-rhIL-2 and (GalNAc)$_3$-rhIL-2 in the liver were 3.5 times and 6.2 times that of rhIL-2 respectively. Further, the concentration of ASOR in the plasma was high immediately after the administration, but it disappeared at once. Meanwhile, the concentration thereof in the liver was changed at a higher level than those of (Gal)$_3$-rhIL-2 and (GalNAc)$_3$-rhIL-2.

Further, in order to prove that the accumulation of (Gal)$_3$-rhIL-2 in the liver occurred owing to the binding between the synthetic ligand (Gal)$_3$ and the asialoglycoprotein receptor present on the surface of the hepatocyte, the test for inhibition of accumulation was conducted though the simultaneous administration of asialoorosomucoid (ASOR) prepared by the method of Bider et al. (Eur. J. Biochem., (1995), 230, 207–212).

That is, 50 μg/kg (calculated as IL-2) of (Gal)$_3$-rhIL-2 and 1,322μg/kg (10 equivalents of IL-2) of ASOR were administered to mice (C57BL/6, CRJ, 6W, male) simultaneously. After 2 minutes, the blood was sampled, and the main organs (liver, kidney and lung) were extracted. The concentrations of the specimens were measured through ELISA, and compared to those of rhIL-2 and (Gal)$_3$-rhIL-2 administered simultaneously.

Figure 6:
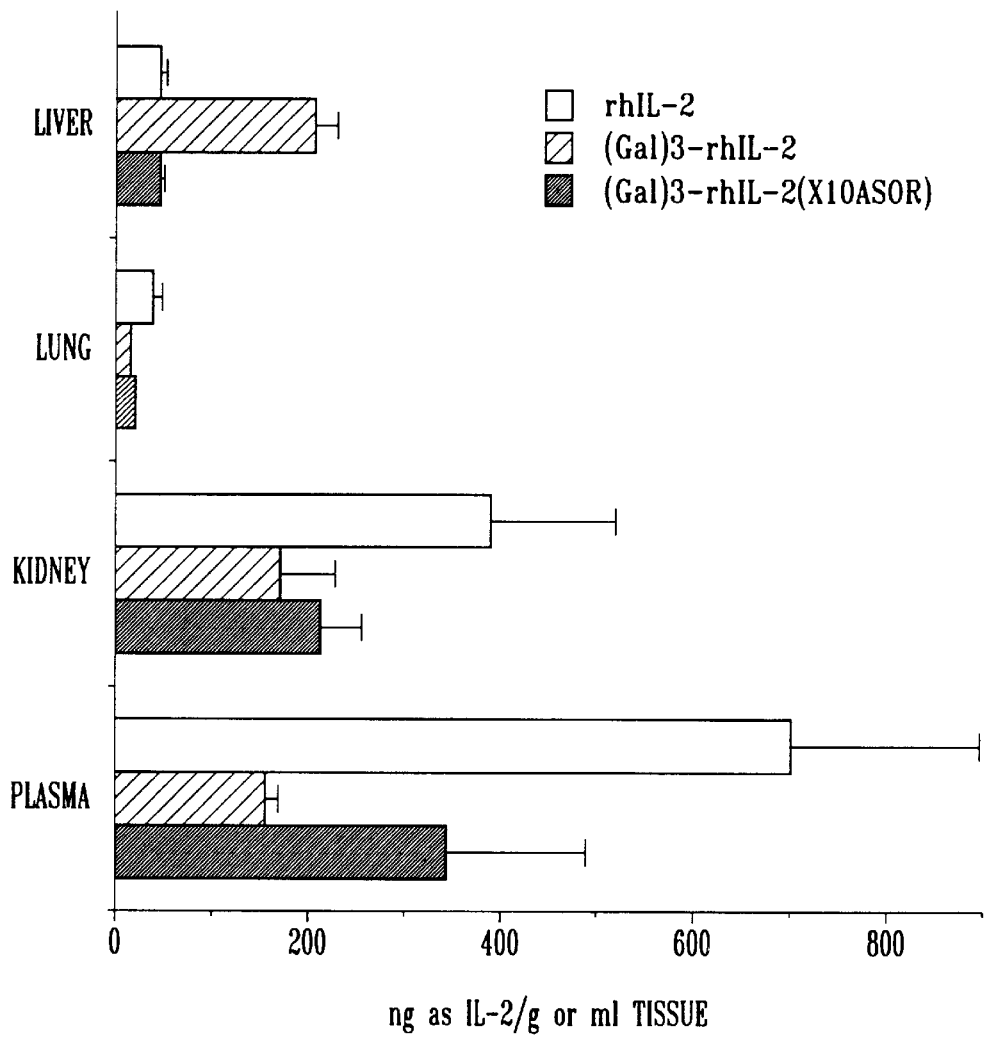
FIG. 6 is a graph showing an amount of $(Gal)_3$-rhIL-2 in the organs by the simultaneous administration of ASOR.

Consequently, as shown in FIG. 6, the amount of (Gal)$_3$-rhIL-2 accumulated in the liver through the simultaneous administration of ASOR was decreased at the same level as that of rhIL-2. It was thus identified that the above-mentioned accumulation of (Gal)$_3$-rhIL-2 was conducted through ASGR.

Further, with respect to (Gal)$_3$-INF-α, the test for inhibition of accumulation in the liver through the simultaneous administration of ASOR was conducted in the same manner. That is, 50 μg/kg (calculated as INF) of (Gal)$_3$-INF-α and 1,051 μg/kg (10 equivalents) of ASOR were administered to mice (C57BL/6) simultaneously. After 2 minutes, the blood was sampled, and the main organs (liver and kidney) were extracted. The concentrations of the specimens were measured through ELISA, and compared to the concentrations of INF-α and (Gal)$_3$-INF-α.

Figure 7:
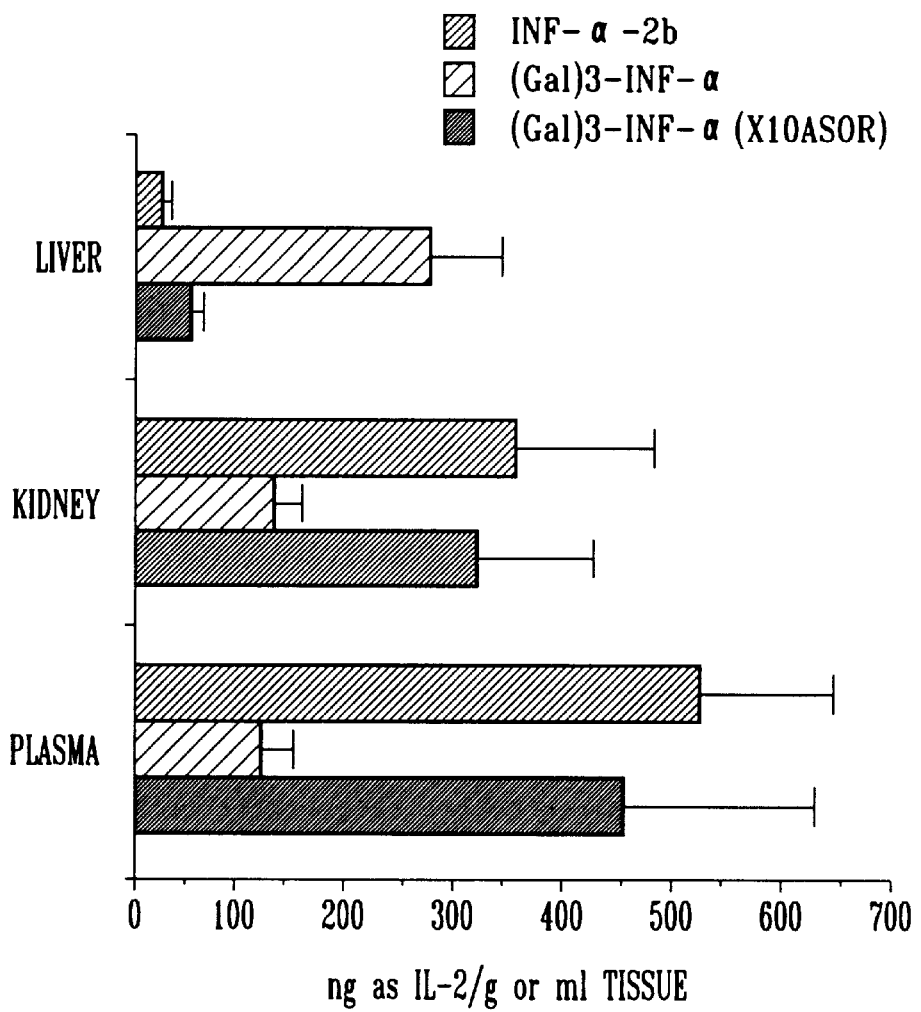
FIG. 7 is a graph showing an amount of $(Gal)_3$-INF-α by the simultaneous administration of ASOR.
Figure 8A:
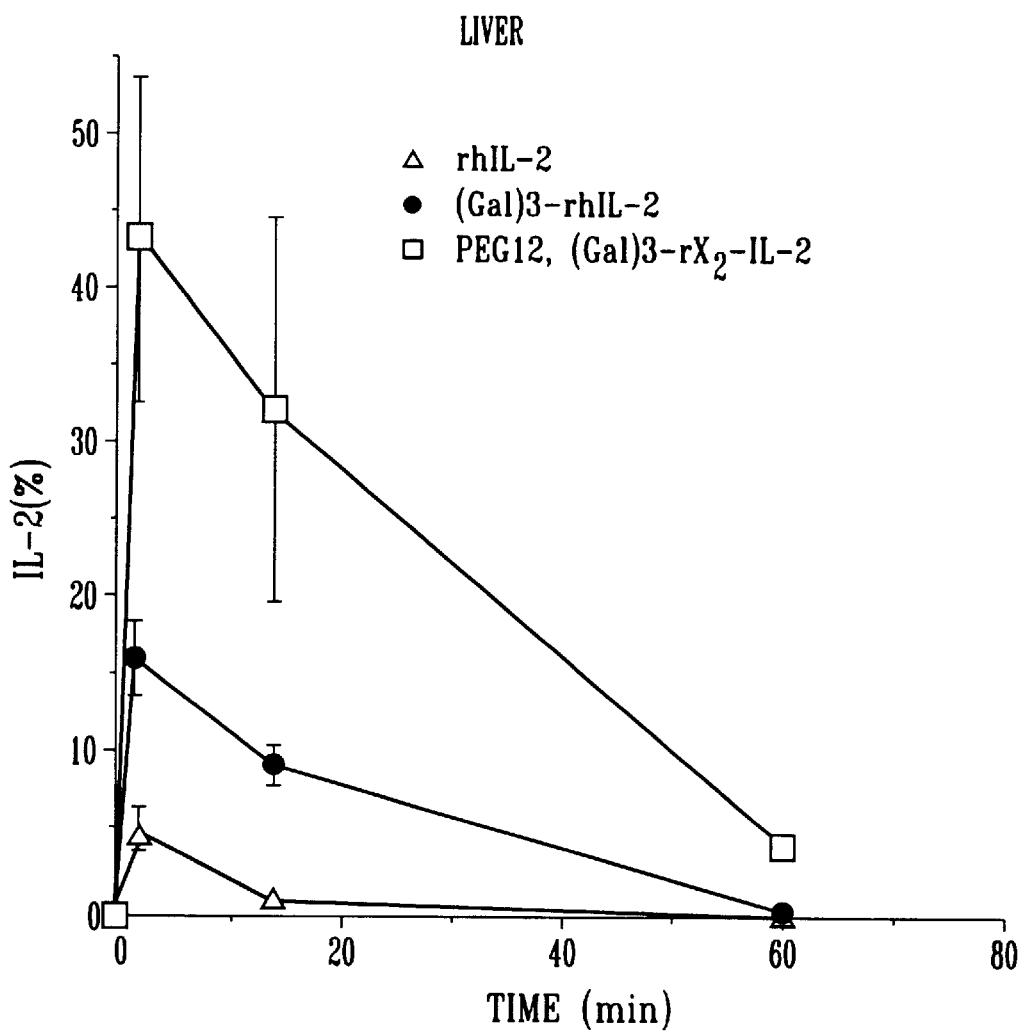
FIGS. 8A–8B are a graph showing a change in the amount of PEG12, $(Gal)_3$-rX-2-IL-2 in the plasma and the liver.
Figure 8B:
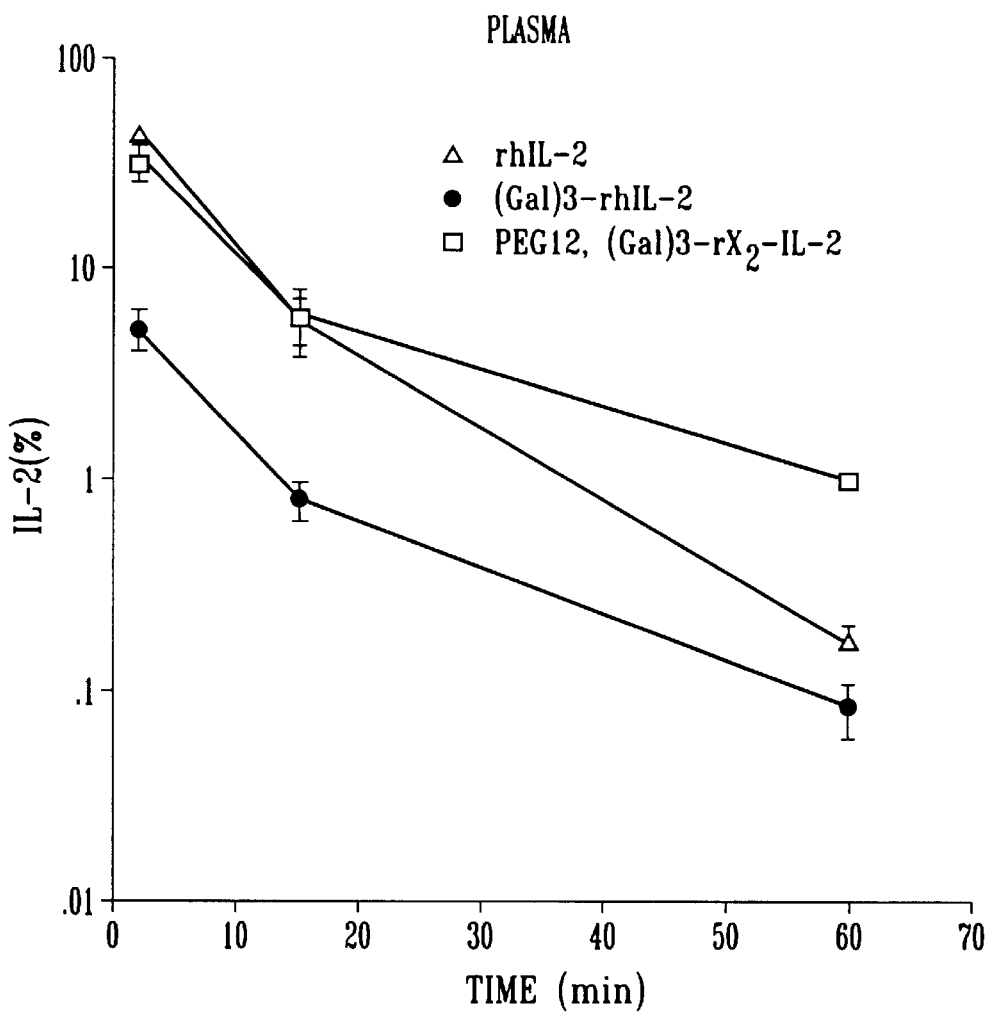

Consequently, as shown in FIG. 7, the amount of (Gal)$_3$-INF-α in the liver, like that of (Gal)$_3$-rhIL-2, was increased to approximately 6 times that of the unmodified INF-α. Further, the amount of (Gal)$_3$-INF-α accumulated in the liver was decreased at the same level as that of unmodified INF-α through the simultaneous administration of ASOR. Thus, it was identified that the above-mentioned accumulation was conducted through ASGR.

Meanwhile, with respect to the chemotherapeutic fate of PEG12, (Gal)$_3$-rX2-IL-2 as well, 33 μg/kg (calculated as IL-2) of the specimen were intravenously administered to mice (C57BL/6, CRJ, 6W, male). After fixed periods of time (2 min, 15 min and 60 min), the blood was sampled, and the liver was extracted. The plasma was sampled in the usual manner. The concentrations of the specimens were measured through ELISA. The liver was homogenized with the addition of PBS (–) in a 9-fold amount, and centrifuged at 3,000 rpm for 5 minutes. Subsequently, the supernatant was diluted with an ELISA buffer, and the concentration of the specimen in the tissue was measured through ELISA. The comparison was conducted at a ratio per amount administered.

As a result, the concentration of PEG12, (Gal)$_3$-rX2-IL-2 in the plasma was changed at a higher level than that of rhIL-2. The concentration of PEG12, (Gal)$_3$-rX2-IL-2 in the liver was changed at by far a higher rate than (Gal)$_3$-rhIL-2, and AUC (area under the concentration curve) in the liver thereof was approximately 12 times that of rhIL-2.

Example 11

Test for Binding of a Modified Product to Hepatocytes

The test for binding of a modified product to hepatocytes was conducted using mouse-separated hepatocytes prepared by the collagenase reflux method which is a modification of the method of Berry et al. (M. N. Berry et al., J. Cell Biol., 43, 506–520 (1969)). That is, seven mice (C57BL/6, 7W, male) were refluxed with a collagenase (type I, supplied by Wako Pure Chemical Industries, Ltd.) and each liver thereof was then severed. Each liver was filtered using a cell filter. Hepatocytes were then collected through centrifugation at a low rate (50 g×1 min), and incubated for from 1 to 4 hours in a D-MEM medium containing 10% FBS (supplied by Gibco, containing 100 U/ml of penicillin, 100 μg/ml of streptomycin and 50 μg/ml of gentamicin) using a tissue culture dish of 150 mm (supplied by Iwaki Garasu K.K.). Only the cells adhered to the tissue surface were treated with a collagenase, and collectively centrifuged at a low rate of three times (50 G×1 min) to purify hepatocytes (total of 1.1×10$^8$ cells, bioavailability 93%). On a 6-well collagenase coated plate, the hepatocytes at concentrations of 8×10$^5$ cells/well were incubated overnight at 37° C. in the above-mentioned 10% FBS containing D-MEM medium, and used in the binding test.

The hepatocyte binding test was conducted by the method of Chang et al. (T. Chang et al., BBA 942. 57–64 (1988)). The cells which were approximately in the almost confluent state were washed twice with a 10 mM CaCl$_2$-containing D-PBS, and the 0.1% BSA-containing buffer was added thereto. The incubation was conducted at 4° C. for 30 minutes. One milliliter of (Gal)$_3$-Tyr-Boc (1.80×10$^5$ cpm/μg), (GalNAc)$_3$-Tyr-Boc (1.49×10$^5$ cpm/mg) or ASOR (3.16×10$^6$ cpm/μg) at various concentrations (dissolved in the 0.1% BSA-containing buffer) which had been $^{125}$I-labeled by the chloramine method was added thereto, and the mixture was incubated at 4° C. for 2 hours. Meanwhile, the non-specific binding was conducted by adding 87.5 mM N-acetylgalactosamine (supplied by Sigma) to the above-mentioned labeled solution. The cells incubated were washed twice with D-PBS cooled at 4° C. Subsequently, the plate was allowed to stand at –20° C. for 30 minutes or more. Thereafter, the radioactivity by the non-specific binding was subtracted from the radioactivity of 0.8 ml of 1 ml of the 0.1 N NaOH solution containing 0.5% SDS, and the radioactivity of the total amount thereof was calculated from the above-obtained value. The thus-calculated value was defined as an amount of a bound fraction. The binding test was conducted at each point of n=2. The total protein amount of the cells was calculated by the Lorry method using 0.1 ml of the solution.

[Bound amount/unbound amount] (liter/mg cell protein) to [bound amount] (pmol/mg cell protein) was Scatchard-plotted. As a result, the plot was in the hyperbolic curved state in all specimens, and it was found that there were two types of bindings. Assuming that there were two types of binding sites which do not interact with each other, the Scatchard analysis which was an application of the method of least squares using the Gauss-Mewton method was conducted, and the specimens were compared with respect to the dissociation constant (Kd1) of their high affinity. Consequently, Kd of ASOR was approximately 0.8 nM, while those of (Gal)$_3$-Tyr-Boc and (GalNAc)$_3$-Tyr-Boc were in the order level of multi-ten nM, and that of (GalNAc)$_3$-Tyr-Boc was lower than that of (Gal)$_3$-Tyr-Boc. Therefore, the two types of synthetic ligands produced exhibited the lower binding affinity for ASGR compared to ASOR having the natural sugar chain-type ligand by the order of approximately 2. Its intensity was found to be in the order of ASOR>>(GalNAc)$_3$>(Gal)$_3$.

Example 12

Uptake of a Modified Product Into Hepatocytes

The test for binding of a modified product into hepatocytes was conducted, like the binding test, using cells obtained by incubating hepatocytes (total of 6.0×10$^7$ cells, bioavailability 92%) formed by refluxing 3 mice (C57BL/6, 9W, male) with a collagenase and purifying them through centrifugation at a low rate, on a collagenase-coated plate in amounts of 6×10$^5$ cells/well in a 10% FBS-containing D-MEM medium (supplied by Gibco, containing 100 U/ml of penicillin, 100 μg/ml of streptomycin and 50 μg/ml of gentamicin) overnight at 37° C. in 5% CO$_2$.

The test for uptake into hepatocytes was also conducted according to the method of Chang et al (T. Chang et al., BBA 942. 57–64 (1988)). The cells which were approximately in the almost confluent state were washed once with a D-MEM medium (pH 7.4) containing 0.1% BSA and 10 mM Hepes, and the buffer was added thereto. The mixture was incubated in 5% $CO_2$ at 37° C. for 30 minutes. One milliliter of 24 nM of $(Gal)_3$-rhIL-2 ($1.14 \times 10^7$ cpm/μg (calculated as IL-2)), $(GalNAc)_3$-rhIL-2 ($1.09 \times 10^7$ cpm/μg (calculated as IL-2)) or ASOR ($3.16 \times 10^6$ cpm/μg) (dissolved in the buffer) which had been $^{125}$I-labeled by the chloramine T method was added thereto, and the incubation was conducted at 37° C. for fixed periods of time (0 minute, 30 minutes, 1 hour, 2 hours and 4 hours). On the other hand, the non-specific uptake was conducted by adding 100 mM N-acetylgalactosamine in each of the labeled solutions. Each plate incubated was moved on an ice bath after the reaction. A part of the medium was sampled, and a D-PBS solution (free from $Ca^{2+}$ and $Mg^{2+}$) containing 20 mM EGTA cooled at 4° C. was added thereto. The mixture was allowed to stand for 5 minutes. This washing was repeated twice. Further, the plate was washed once with a D-PBS solution (free from $Ca^{2+}$ and $Mg^{2+}$) cooled, and then allowed to stand at −20° C. for 30 minutes or more. The radioactivity by the non-specific binding was subtracted from the radioactivity of 0.8 ml of 1 ml of the 0.1 N NaOH solution containing 0.5% SDS in each well, and the radioactivity of the total amount thereof was calculated from the above-obtained value. The thus-calculated value was defined as an amount of an uptake fraction. Meanwhile, a value obtained by subtracting the radioactivity by the non-specific degradation from the radioactivity of the total trichloroacetic acid-soluble fraction in the medium was defined as an amount of a degradation fraction. The uptake tast was conducted with each point of n=3. The total protein amount of the cells was calculated by the Lorry method with respect to 0.1 ml of the solution.

Figure 9A:
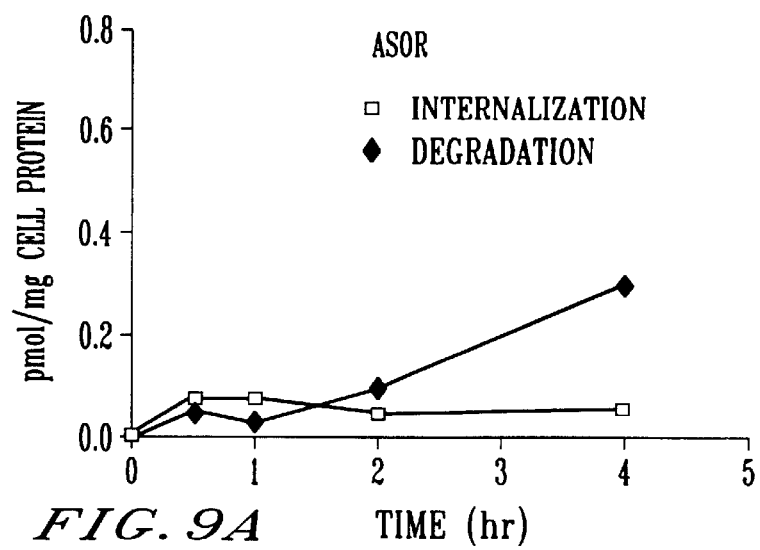
FIGS. 9A–9C are a graph showing a change in the uptake of $(Gal)_3$-rhIL-2 and $(GalNAc)_3$-rhIL-2 in the mouse separated hepatocyte and the amount decomposed thereof.

Consequently, with respect to ASOR, as shown in FIG. 9(A), the uptake component was observed after 30 minutes of the incubation, and the saturation was reached in 1 hour. The degradation component was gradually increased with the lapse of time, and the amount was the highest after 4 hours.

Figure 9B:
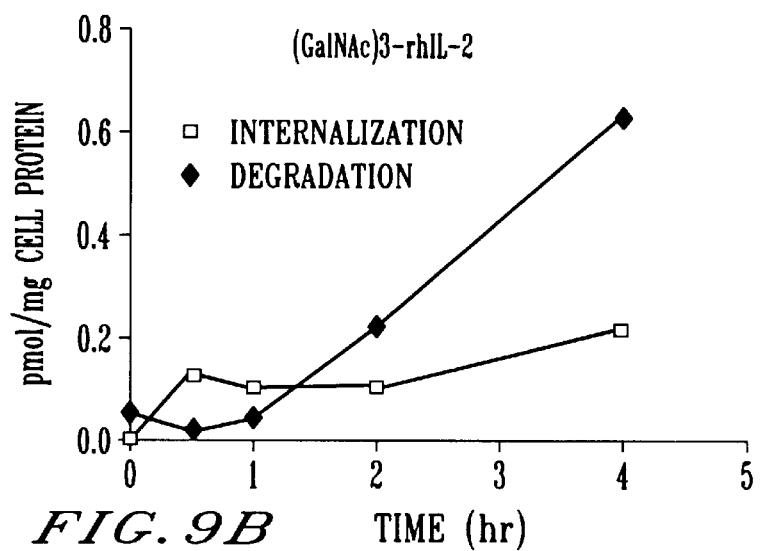
Figure 9C:
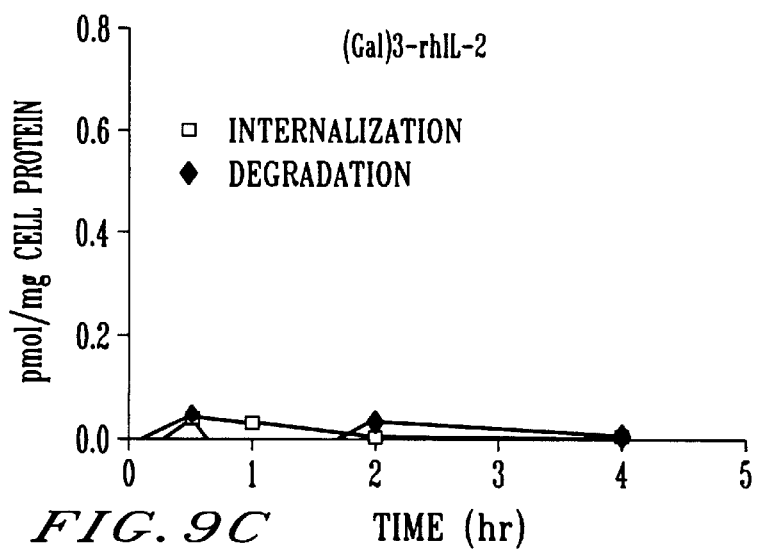

Meanwhile, with respect to $(Gal)_3$-rhIL-2, as shown in FIG. 9(C), the uptake and degradation components were scarcely observed, and it was identified that $(Gal)_3$-rhIL-2 was hardly taken up in hepatocytes compared to ASOR. As a result, it proved that the binding affinity of the ligand for ASGR present specifically in hepatocytes was decreased by the order of approximately 2, thereby making it possible to impart the property that its modified product could be accumulated into the liver upon recognizing the receptor though intravenous administration but was hardly taken up into hepatocytes.

$(GalNAc)_3$-rhIL-2 was found to be taken up in a relatively short period of time as shown in FIG. 9(B). As is clear from the above-mentioned test, since $(GalNAc)_3$-rhIL-2 exhibited a low affinity for ASGR, it was found to be preferably used as a DDS preparation of a medication which is required to be selectively arrived at the liver and metabolized at a relatively early stage.

Example 13

Antitumor Effect of a Modified Product

Figure 10:
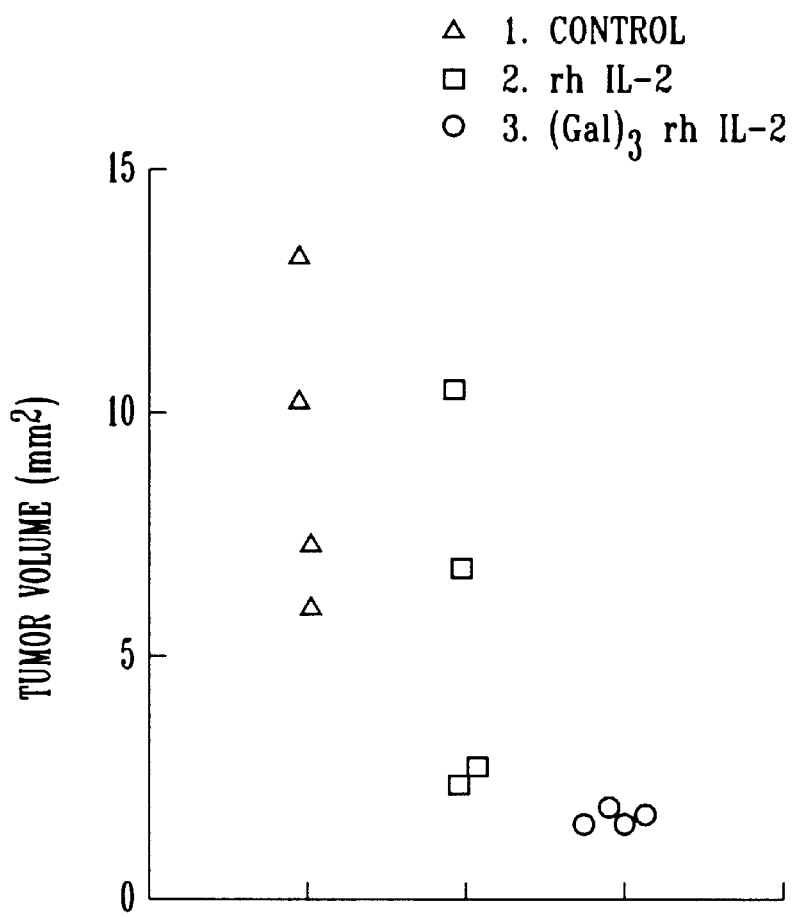
FIG. 10 shows an effect of $(Gal)_3$-rhIL-2 in S908.D2.vp2 liver transplanted mouse.

Mice (B10D2, 6W, female) in which a fibrosarcoma (S908, D2. vp2) was implanted in the liver ($7.5 \times 10^4$ cells/mouse) were used in this test. On Day 7 after the implantation, $(Gal)_3$-rhIL-2 and rhIL-2 were intravenously administered five times in total (0.5 μg/shot) (n=4). On Day 28, the anatomical examination was conducted. Consequently, as shown in FIG. 10, the tumor was remarkably minimized in the $(Gal)_3$-rhIL-2-administered group as compared to the rhIL-2-administered group. Thus, it proved that the antitumor effect of $(Gal)_3$-rhIL-2 was enhanced as compared to that of rhIL-2.

Example 14

Toxicity of a Modified Product

In the experiment, each of $(Gal)_3$-rhIL-2 and rhIL-2 was intravenously administered to mice (B10D2, 6W, female) twice a day continuously for 5 days (n=3) (1.5 μg/day, 4.4 μg/day, 13.3 μg/day, 40 μg/day; the concentrations were all calculated as IL-2). After 2 hours of the final administration, the anatomical examination was conducted. As evaluation items, the organ weights (wet weights) of the liver, the lung and the kidney were measured, and the serum was collected. Then, the blood biochemical test was carried out using Fuji Dry Chem.

Consequently, as shown in FIG. 11, the organ weight (% (w/w)) of $(Gal)_3$-rhIL-2 in the lung tended to increase at a lower rate than that of rhIL-2 at the same dose. In the 40 μg/day administration group, rhIL-2 showed the significant increase as compared to the physiological saline administration group as a control. Whereas, no significant increase was observed in $(Gal)_3$-rhIL-2. On the other hand, in the liver, the increase in the organ weight % was observed with the increase in the dose of $(Gal)_3$-rhIL-2 and rhIL-2. In the 40 μg/day administration group, rhIL-2 and $(Gal)_3$-rhIL-2 exhibited the significant increase as compared to the physiological saline administration group as a control. However, no big difference was found therebetween. Further, in the kidney, even though the doses of $(Gal)_3$-rhIL-2 and rhIL-2 were increased, no increase in the organ weight was observed.

On the other hand, as a result of the blood biochemical examination, as shown in FIG. 12, in GOT (glutamic oxaloacetic transaminase), GPT (glutamic pyruvic transaminase) and TBIL-S (total bilirubin), the increase in the measured value was observed in $(Gal)_3$-rhIL-2 and rhIL-2 with the increase in the doses thereof, and rhIL-2 tended to show a higher value. Meanwhile, in TP-S (total protein), AlB-S (albumin) and BUN-S (blood urea nitrogen), no increase in the measured value with the increase in the dose was observed.

From the above-mentioned results, it was found that the toxicity of $(Gal)_3$-rhIL-2 was lower than that of rhIL-2 in the lung and no increase was observed in the liver and the kidney, with the result that the modified product of the present invention was accumulated in the liver without imparting the toxicity to the other organs.

What is claimed is:

1. A process for producing a modified physiologically active protein comprising:

(a) reacting a physiologically active protein with a terminal amino group of a branched chain ligand, in the presence of transglutaminase obtained from a microorganism, for a time and under conditions effective to form an amide bond between the γ-carboxamide group of a glutamine residue in said protein and the terminal amino group in said branched chain ligand;

wherein the physiologically active protein has a molecular weight of 1–200 kD and contains at least one glutamine residue;

the branched chain ligand contains a galactose (Gal) or N-acetyl galactosamine (GalNac) group and an amino acid derivative containing an amino group, and said ligand bears a terminal amino group which becomes a substrate for the transglutaminase; and (b) isolating the modified physiologically active protein, of which binding affinity for an asialoglycoprotein receptor present on the surface of a hepatocyte is lower than the binding affinity of an asialoorosomucoid for said receptor, with the proviso that said branched chain ligand is other than that of formula (V) or (XVIII)

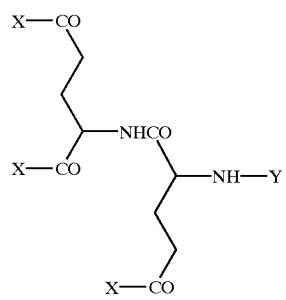

(V)

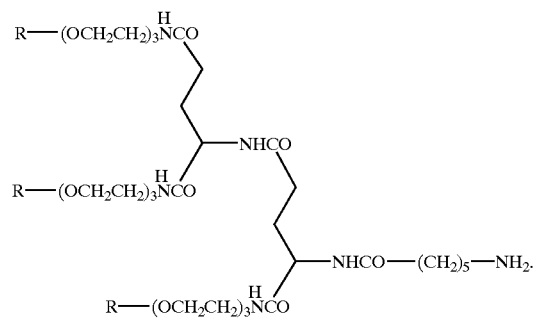

(XVIII)

2. The process for producing the modified physiologically active protein of claim 1, wherein the branched-chain ligand is a galactose (Gal) or N-acetylgalactosamine (GalNAc)-containing amino acid derivative represented by

Z—AA—W    (I)

wherein
- AA represents one or two basic or acidic amino acids, in which Z or W may be an N-terminus, and when AA is two amino acids, they may have an amido bond between each other, in which the reaction site of each amino acid is independently selected from an alpha position amino group, an alpha position carboxyl group, a side chain amino group, and a side chain carboxyl group;
- W is an alkylamine derivative represented by the formula —$X^1$—$(CH_2)_n$—$NH_2$ in which n is an integer of from 1 to 8, $X^1$ represents —CO— when W is bonded to an amino group of an amino acid represented by AA, and represents —NH— when W is bonded to a carboxyl group of an amino acid represented by AA;
- Z is a Gal- or GalNAc-containing group represented by the formula $X^2$—$(CH_2CH_2O)_p$—R or the formula —$X^2$—$(CH_2)_q$—OR in which R represents Gal or GalNAc, p is an integer of from 1 to 6, q is an integer of from 1 to 18, $X^2$ represents —CO— when Z is bonded to an amino group of an amino acid represented by AA, and represents —NH— when Z is bonded to a carboxyl group of an amino acid represented by AA.

3. The process of claim 2, wherein AA represents two amino acids that are bonded together in an amide linkage and wherein the amide linkage is between the alpha-amino group of one amino acid and the alpha-carboxyl group of the other amino acid.

4. The process of claim 2, wherein AA represents two amino acids, each independently selected from glutamic acid and aspartic acid, and wherein there is an amide bond between the alpha-amino group of one amino acid and the side chain carboxyl group of the other amino acid.

5. The process of claim 2, wherein the branched chain ligand is a ligand represented by one of a formula selected from the group consisting of (II), (III), (VI), (VII), (VIII), (IX), (X), (XI), (XII), (XIII), (XIV), and (XV):

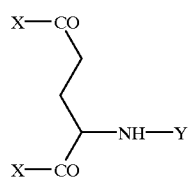

(II)

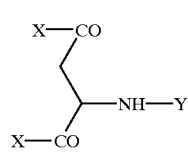

(III)

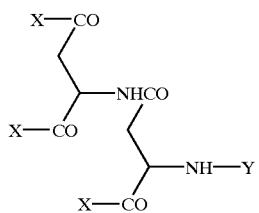

(VI)

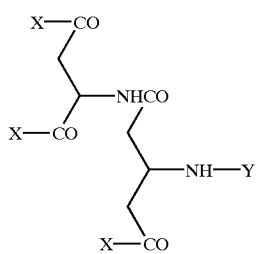

(VII)

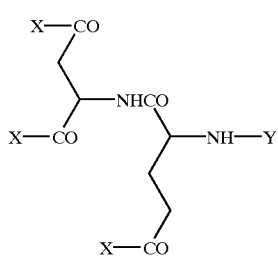

(VIII)

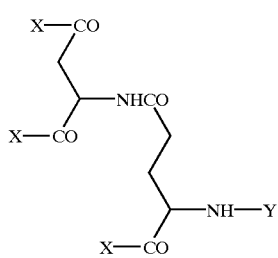

(IX)

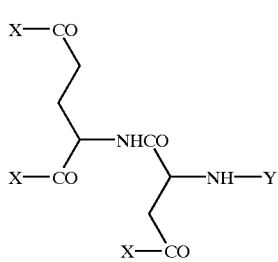

(X)

-continued

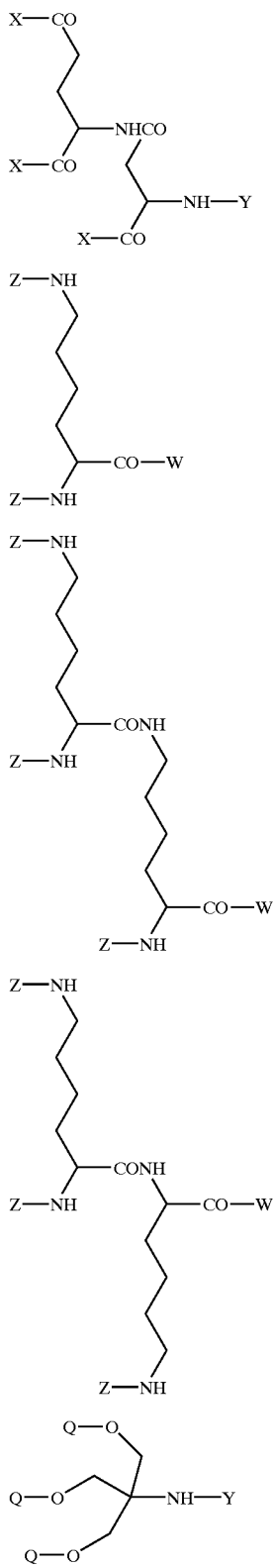

wherein
X represents R—(OCH$_2$CH$_2$)$_p$—NH— or R—O(CH$_2$)$_q$—NH— in which R represents galactose or N-acetylgalactosamine, p is an integer of from 1 to 6, and q is an integer of from 1 to 18, and Y represents —CO(CH$_2$)$_n$NH$_2$ in which n is an integer of from 1 to 8;

Z represents R(OCH$_2$CH$_2$)$_p$CO— or R—O(CH$_2$)$_q$CO— in which R represents galactose or N-acetylgalactosamine, p is an integer of from 1 to 6, and q is an integer of from 1 to 18;

W represents —NH(CH$_2$)$_n$NH$_2$ in which n is an integer of from 1 to 8;

Q represents R(OCH$_2$CH$_2$)$_p$— or R—O(CH$_2$)$_q$— in which R represents galactose or N-acetylgalactosamine, p is an integer of from 1 to 6, and q is an integer of from 1 to 18.

6. A modified physiologically active protein produced by the process of claim 1, wherein said physiologically active protein is a cytokine.

7. The modified physiologically active protein of claim 6, wherein the protein has a liver accumulation property.

8. The modified physiologically active protein of claim 6, wherein the physiologically active protein is interleukin-2 (IL-2) or interferon-α (IFN-α).

9. The modified physiologically active protein of claim 6, wherein the branched-chain ligand is a galactose (Gal) or N-acetylgalactosamine (GalNAc)-containing amino acid derivative represented by formula (I)

$$Z—AA—W \quad (I)$$

wherein
AA represents one or two basic or acidic amino acids, in which Z or W may be an N-terminus, and when AA is two amino acids, they may have an amide bond between each other, in which the reaction site of each amino acid is independently selected from an alpha position amino group, an alpha position carboxyl group, a side chain amino group, and a side chain carboxyl group;

W is an alkylamine derivative represented by the formula —X$^1$—(CH$_2$)$_n$—NH$_2$ in which n is an integer of from 1 to 8, X$^1$ represents —CO— when W is bonded to an amino group of an amino acid represented by AA, and represents —NH— when W is bonded to a carboxyl group of an amino acid represented by AA, and Z is a Gal- or GalNAc-containing group represented by the formula X$^2$—(CH$_2$CH$_2$O)$_p$—R or the formula —X$^2$—(CH$_2$)$_q$—OR in which R represents Gal or GalNAc, p is an integer of from 1 to 6, q is an integer of from 1 to 18, X$^2$ represents —CO— when Z is bonded to an amino group of an amino acid represented by AA, and represents —NH— when Z is bonded to a carboxyl group of an amino acid represented by AA.

10. The modified physiologically active protein of claim 9, wherein the group AA of the branched-chain ligand represented by formula (I) is one or two amino acids independently selected from the group consisting of glutamic acid and aspartic acid.

11. The modified physiologically active protein of claim 9, wherein AA represents two amino acids that are bonded together in an amide linkage and wherein the amide linkage is between the alpha-amino group of one amino acid and the alpha-carboxyl group of the other amino acid.

12. The modified physiologically active protein of claim 9, wherein AA represents two amino acids, each independently selected from the group consisting of glutamic acid and aspartic acid, and wherein there is an amide bond between the alpha-amino group of one amino acid and the side chain carboxyl group of the other amino acid.

13. The modified physiologically active protein of claim 9, wherein the branched chain ligand is a ligand represented by one of a formula selected from the group consisting of (II), (III), (VI), (VII), (VIII), (IX), (X), (XI), (XII), (XIII), (XIV), and (XV):
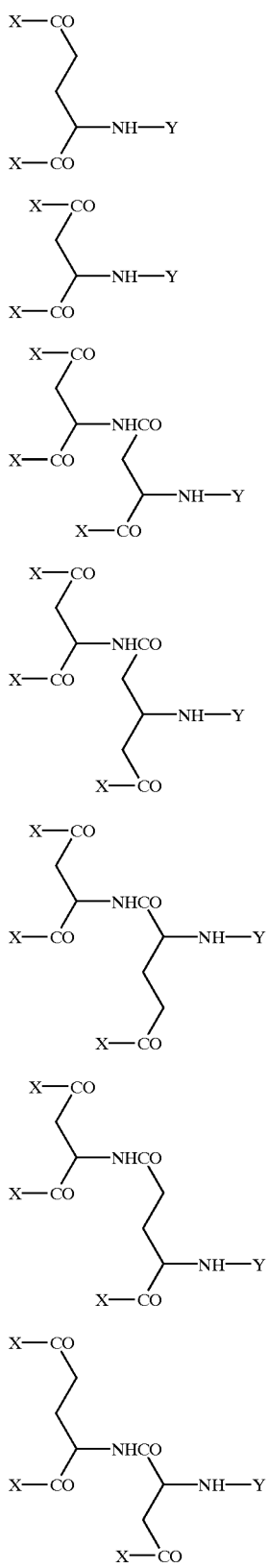
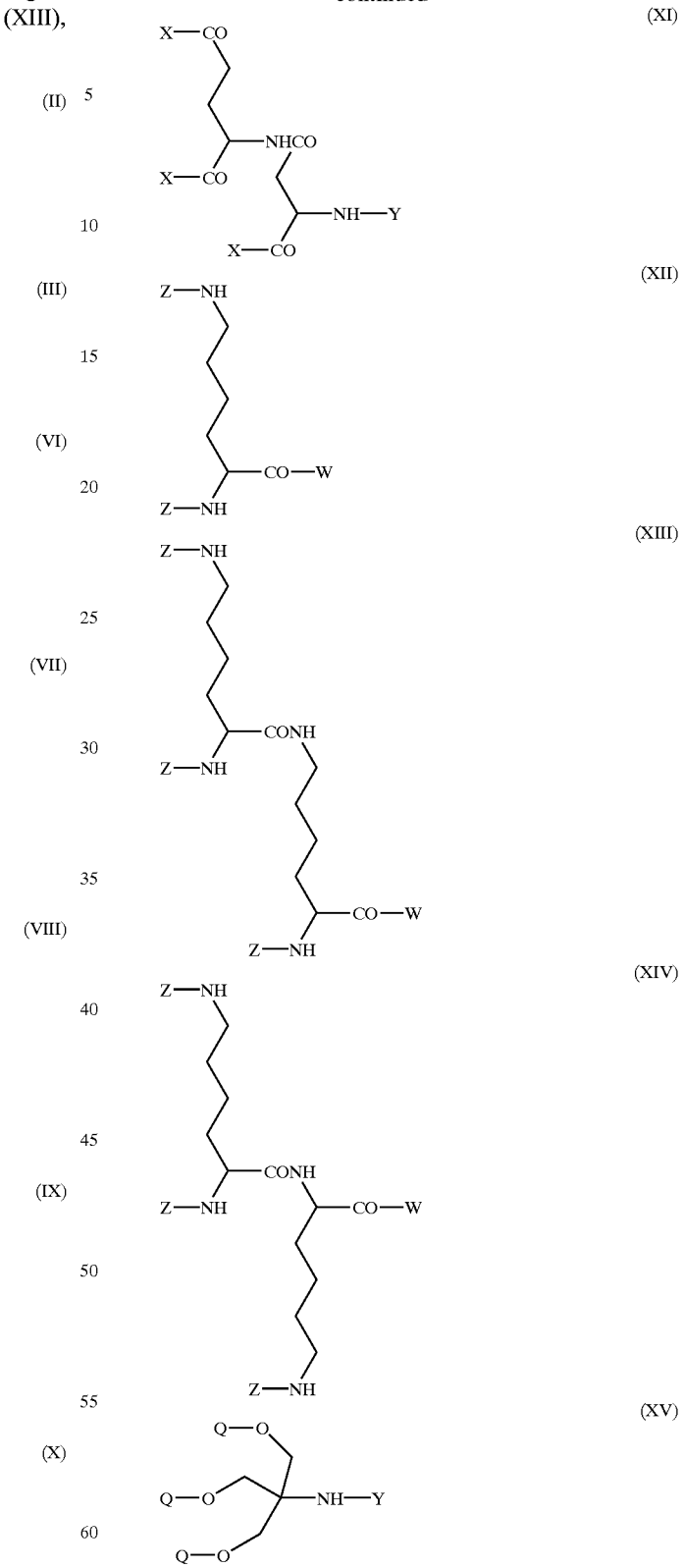
wherein
X represents R—(OCH$_2$CH$_2$)$_p$—NH— or R—O—(CH$_2$)$_q$—NH— in which R represents galactose or N-acetylgalactosamine, p is an integer of from 1 to 6, and q is an integer of from 1 to 18;

Y represents —CO(CH$_2$)$_n$NH$_2$ in which n is an integer of from 1 to 8;

Z represents R(OCH$_2$CH$_2$)pCO— or R—O(CH$_2$)$_q$CO— in which R represents galactose or N-acetylgalactosamine, p is an integer of from 1 to 6, and q is an integer of from 1 to 18;

W represents —NH(CH$_2$)$_n$NH$_2$ in which n is an integer of from 1 to 8; and

Q represents R(OCH$_2$CH$_2$)$_p$— or R—O(CH$_2$)$_q$— in which R represents galactose or N-acetylgalactosamine, p is an integer of from 1 to 6, and q is an integer of from 1 to 18.

14. A pharmaceutical composition comprising the modified physiologically active protein of claim 6, and a pharmaceutically acceptable carrier.

15. The pharmaceutical composition of claim 14, wherein the physiologically active protein is interleukin-2 (IL-2) or interferon-α (IFN-α).

16. The pharmaceutical composition of claim 14, wherein the branched-chain ligand is a galactose (Gal) or N-acetylgalactosamine (GalNAc)-containing amino acid derivative represented by formula (I)

Z—AA—W   (I)

wherein

AA represents one or two basic or acidic amino acids, in which Z or W may be an N-terminus, and when AA is two amino acids, they may have an amide bond between each other, in which the reaction site of each amino acid is independently selected from the group consisting of an alpha position amino group, an alpha position carboxyl group, a side chain amino group, and a side chain carboxyl group;

W is an alkylamine derivative represented by the formula —X$^1$—(CH$_2$)$_n$—NH$_2$ in which n is an integer of from 1 to 8, X$^1$ represents —CO— when W is bonded to an amino group of an amino acid represented by AA, and represents —NH— when W is bonded to a carboxyl group of an amino acid represented by AA; and Z is a Gal- or GalNAc-containing group represented by the formula X$^2$—(CH$_2$CH$_2$O)$_p$—R or the formula —X$^2$—(CH$_2$)$_q$—OR in which R represents Gal or GalNAc, p is an integer of from 1 to 6, q is an integer of from 1 to 18, X$^2$ represents —CO— when Z is bonded to an amino group of an amino acid represented by AA, and represents —NH— when Z is bonded to a carboxyl group of an amino acid represented by AA.

17. The pharmaceutical composition of claim 16, wherein AA represents two amino acids that are bonded together in an amide linkage and wherein the amide linkage is between the alpha-amino group of one amino acid and the alpha-carboxyl group of the other amino acid.

18. The pharmaceutical composition of claim 16, wherein AA represents two amino acids, each independently selected from glutamic acid and aspartic acid, and wherein there is an amide bond between the alpha-amino group of one amino acid and the side chain carboxyl group of the other amino acid.

19. The pharmaceutical composition of claim 16, wherein the group AA of the branched-chain ligand of formula (I) is one or two amino acids independently selected from the group consisting of glutamic acid and aspartic acid.

20. The pharmaceutical composition of claim 16 wherein the branched chain ligand is a ligand represented by one of a formula selected from the group consisting of (II), (III), (VI), (VII), (VIII), (IX), (X), (XI), (XII), (XIII), (XIV), and (XV):

(II)

(III)

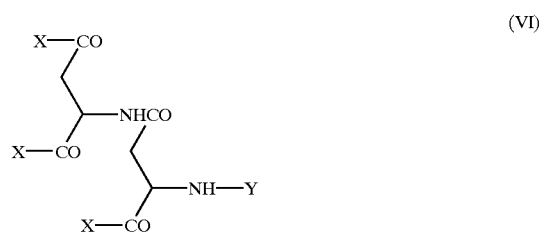

(VI)

(VII)

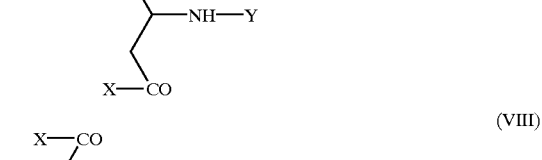

(VIII)

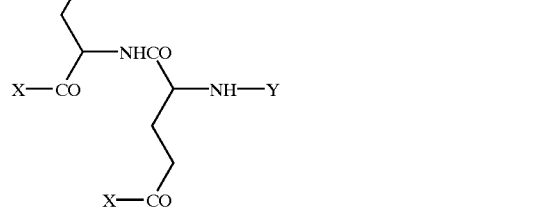

(IX)

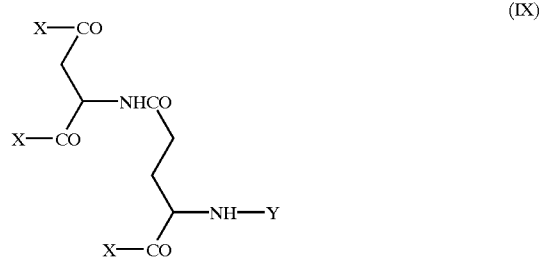

(X)

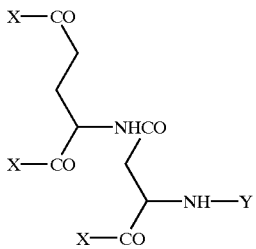
(XI)

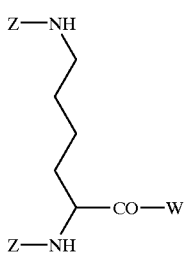
(XII)

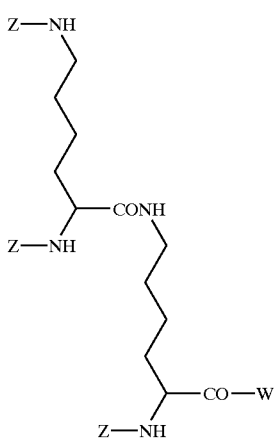
(XIII)

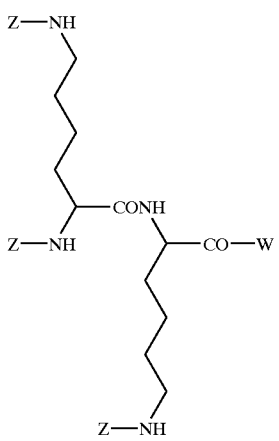
(XIV)

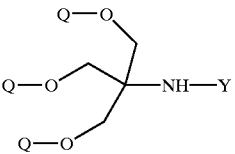
(XV)

wherein

X represents R—(OCH$_2$CH$_2$)$_p$—NH— or R—O(CH$_2$)$_q$—NH— in which R represents galactose or N-acetylgalactosamine, p is an integer of from 1 to 6, and q is an integer of from 1 to 18;

Y represents —CO(CH$_2$)$_n$NH$_2$ in which n is an integer of from 1 to 8;

Z represents R(OCH$_2$CH$_2$)$_p$CO— or R—O(CH$_2$)$_q$CO— in which R represents galactose or N-acetylgalactosamine, p is an integer of from 1 to 6, and q is an integer of from 1 to 18, and W represents —NH(CH$_2$)$_n$NH$_2$ in which n is an integer of from 1 to 8; and Q represents R(OCH$_2$CH$_2$)$_p$— or R—O(CH$_2$)$_q$— in which R represents galactose or N-acetylgalactosamine, p is an integer of from 1 to 6, and q is an integer of from 1 to 18.

21. A process for producing a modified physiologically active protein comprising reacting a physiologically active protein with a terminal amino group of a first ligand, in the presence of a first transglutaminase, for a time and under conditions effective to form an amide bond between the γ-carboxamide group of a glutamine residue in said physiologically active protein and the terminal amino group of said first ligand;

(a) reacting said modified protein with an amino group of a second ligand in the presence of a second transglutaminase, for a time and under conditions effective to form an amide bond between the γ-carboxamide group of a glutamine residue in said protein and the amino group in said second ligand, wherein the first transglutaminase is obtained from a microorganism, and the second transglutaminase is obtained from a source other than a microorganism, the first ligand is a branched-chain ligand which contains a galactose (Gal) or N-acetyl galactosamine (GalNAc) group and an amino acid derivative containing an amino group, and said first ligand bears a terminal amino group which becomes a substrate for the transglutaminase, and the second ligand is structurally distinct from the first ligand, the physiologically active protein has a molecular weight of 1–200 kD and contains at least one glutamine residue, and (b) isolating the modified physiologically active protein, of which binding affinity for an asialoglycoprotein receptor present on the surface of a hepatocyte is lower than the binding affinity of an asialoorosomucoid for said receptor, with the proviso that said branched chain ligand is other than that of formula (V) or (XVIII)

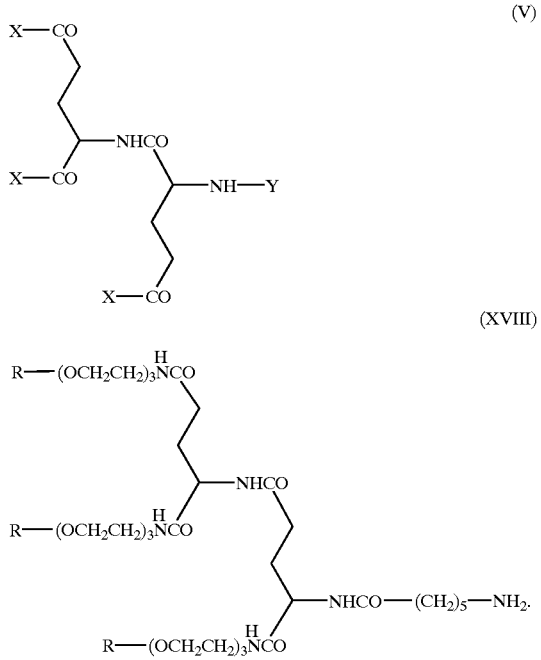

22. The process of claim 21, wherein the second ligand is a polyethylene glycol derivative, and the transglutaminase obtained from a source other than a microorganism is a transglutaminase obtained from an animal.

23. A modified physiologically active protein produced by the process of claim 21, wherein said physiologically active protein is a cytokine.

24. The modified physiologically active protein of claim 21, wherein the physiologically active protein modified with the branched chain ligand is further modified with a transglutaminase other than a transglutaminase obtained from a microorganism, using a ligand other than the branched-chain ligand of claim 21.

25. The modified physiologically active protein of claim 24, wherein the ligand other than the branched-chain ligand is a polyethylene glycol derivative, and the transglutaminase obtained from a source other than a microorganism is a transglutaminase obtained from an animal.

26. A pharmaceutical composition comprising the modified, physiologically active protein of claim 23 and a pharmaceutically acceptable carrier.

* * * * *